(12) United States Patent
Jansson et al.

(10) Patent No.: US 11,179,678 B2
(45) Date of Patent: *Nov. 23, 2021

(54) SYSTEM AND METHOD FOR FILTRATION AND/OR DILUTION OF FLUIDS

(71) Applicant: GAMBRO LUNDIA AB, Lund (SE)

(72) Inventors: Olof Jansson, Vellinge (SE); Bjoern Ericson, Lund (SE); Henrik Hall, Lund (SE)

(73) Assignee: GAMBRO LUNDIA AB, Lund (SE)

(*) Notice: Subject to any disclaimer, the term of this patent is extended or adjusted under 35 U.S.C. 154(b) by 63 days.

This patent is subject to a terminal disclaimer.

(21) Appl. No.: 16/622,002

(22) PCT Filed: Jun. 14, 2018

(86) PCT No.: PCT/EP2018/065759
§ 371 (c)(1),
(2) Date: Dec. 12, 2019

(87) PCT Pub. No.: WO2018/229174
PCT Pub. Date: Dec. 20, 2018

(65) Prior Publication Data
US 2020/0122088 A1 Apr. 23, 2020

(30) Foreign Application Priority Data
Jun. 14, 2017 (EP) ..................................... 17176107

(51) Int. Cl.
*B01D 63/02* (2006.01)
*A61M 1/16* (2006.01)
(Continued)

(52) U.S. Cl.
CPC ........... *B01D 63/02* (2013.01); *A61M 1/1621* (2014.02); *A61M 1/267* (2014.02);
(Continued)

(58) Field of Classification Search
CPC ...... B01D 63/02; B01D 61/243; B01D 61/28; B01D 2311/2649; B01D 2313/04;
(Continued)

(56) References Cited

U.S. PATENT DOCUMENTS 4,861,485 A * 8/1989 Fecondini ........... A61M 1/3413
210/641
7,459,084 B2 * 12/2008 Baig ....................... C02F 1/041
210/640

(Continued)

FOREIGN PATENT DOCUMENTS

EP  3178539   6/2017
JP  0386218 A  4/1991

OTHER PUBLICATIONS

PCT Search Report and Written Opinion prepared for PCT/EP2018/065759, completed Dec. 11, 2018.

*Primary Examiner* — Krishnan S Menon
(74) *Attorney, Agent, or Firm* — Barnes & Thornburg LLP

(57) ABSTRACT

The present invention relates to systems and methods for filtration and/or dilution of fluids, in particular for the dialysis of blood. The systems comprise a filter device (10) having a fluid chamber (18) and comprising a first lid (20) having arranged thereon a first fluid port (22). The filter device (10) further comprises a second lid (30) having arranged thereon at least a second fluid port (32). The filter device (10) further comprises a plurality of hollow fibers (40) arranged within the housing (12), wherein each of the plurality of hollow fibers (40) comprises a semi-permeable membrane and defines a fluid channel extending longitudinally through an interior of the respective hollow fiber (40). Also, the filter device (10) comprises a fourth fluid port (50) and a fifth fluid port (52) both provided at the fluid chamber (18).

19 Claims, 9 Drawing Sheets

(51) Int. Cl.
     *A61M 1/26*     (2006.01)
     *A61M 1/34*     (2006.01)
     *B01D 61/24*     (2006.01)
     *B01D 61/28*     (2006.01)

(52) U.S. Cl.
     CPC ........ *A61M 1/3413* (2013.01); *A61M 1/3434* (2014.02); *B01D 61/243* (2013.01); *B01D 61/28* (2013.01); *B01D 2311/2649* (2013.01); *B01D 2313/04* (2013.01); *B01D 2313/21* (2013.01)

(58) Field of Classification Search
     CPC ............ B01D 2313/21; B01D 2313/00; B01D 2313/243; B01D 2315/18; B01D 61/32; B01D 61/58; B01D 63/024; B01D 63/04; A61M 1/1621; A61M 1/267; A61M 1/3434; A61M 1/3413; A61M 1/3646; A61M 1/3649
     See application file for complete search history.

(56) References Cited

U.S. PATENT DOCUMENTS

| | | |
|---|---|---|
| 7,622,041 B2 | 11/2009 | Dannenamier et al. |
| 2002/0053540 A1 | 5/2002 | Collins et al. |
| 2004/0127842 A1 | 7/2004 | Collins et al. |
| 2006/0081525 A1* | 4/2006 | Lobovsky ................ B01J 20/10 210/321.88 |
| 2013/0020250 A1 | 1/2013 | Keller et al. |

* cited by examiner (A)

(B)

SYSTEM AND METHOD FOR FILTRATION AND/OR DILUTION OF FLUIDS

CROSS-REFERENCE TO RELATED APPLICATIONS

This application is the U.S. national phase of PCT/EP2018/065759, filed on Jun. 14, 2018, which claims the benefit of European Patent Application Serial Number 17176107.5, filed on Jun. 14, 2017, the entire disclosures of both of which are incorporated herein by reference.

FIELD OF THE INVENTION

The present invention relates to a system comprising a filter device and to method for filtration and/or dilution of fluids. The system can be applied in dialysis-type treatments and for filtration processes similar to and related to the haemodialysis process, haemodiafiltration and ultrafiltration.

BACKGROUND OF THE INVENTION

Filter devices having hollow fibers are used, for example, in the area of dialysis for a wide variety of purposes. Such filters may thus also be referred to as dialysers, these being used for example in haemodialysis (HD), in which blood is directed into and along the inside of the semi-permeable membranes of the hollow fibers while dialysis fluid is directed around the outside of the hollow fibers. Various convection and diffusion processes may thereby take place across the membranes of the hollow fibers. These processes serve, for example, to purify and to remove excess fluid, in particular waste products such as urinary excreted substances, from the blood. Additionally, the electrolyte concentration in the blood can be adjusted and/or normalized, and buffers such as bicarbonate or acetate can be added to the blood. The HD process is effective at removing substances having a low molecular weight.

The above-mentioned filter devices may generally also be employed in so-called haemofiltration (HF), in which a substitution fluid is added to the blood. According to this process, the blood is directed through the inside of the hollow fibers, although in this case no dialysis fluid is normally passed around the outside of the fibers. Here, excess fluids, in particular plasma water as well as waste products, are removed from the blood by means of a pressure difference across the semi-permeable membranes of the hollow fibers. The substitution fluid can be added either pre or post the filtration unit. This is regarded as, respectively, pre or post dilution HF treatment.

A further application for the present type of filter device includes haemodiafiltration (HDF): a combination of HD and HF, in which dialysate flows on the outside of the hollow fibers while blood flows on the inside of the hollow fibers and, at the same time, a pressure gradient exists across the semi-permeable membrane, i.e. between the inside and the outside of the hollow fibers. Infusion fluid may be added to the blood either prior to or after the filtration. This process can result in a higher filtration rate and is especially effective at removing substances having a low and middle molecular weight.

U.S. Pat. No. 7,622,041 B2 discloses a filter device comprising a housing and two end-caps, one arranged at each end of the housing. The housing comprises a longitudinally extending tubular wall having two opposed ends. A fluid port is provided at each of the two opposed ends for introducing blood from a patient and removing the blood after being filtered. Two additional fluid ports are arranged each on one of the two end-caps, the two additional fluid ports being used for introducing and removing a dialysis fluid. A plurality of hollow fibers is arranged within the housing for directing the introduced blood from one end-cap to the other end-cap.

Although the filter device known from the above-mentioned prior art is able to both filter the blood and purify infusion fluids, the device has a comparatively complicated design by including one or more internal walls inside the housing in order to divide the inner space of the housing into two or more compartments.

SUMMARY OF THE INVENTION

It is an object of the present invention to provide a system comprising a filter device and a method for filtration and/or dilution of fluids which enable easy production of useful fluids such as infusion fluids and/or substitution fluids, easy priming and/or rinsing off process while maintaining the safety and efficiency of filtration.

In a first aspect of the present invention, a system for filtration and/or dilution of fluids is presented that comprises:

a filter device for filtration of fluids, wherein said filter device comprises:

a housing having a first end and a second end and defining a fluid chamber extending between the first end and the second end;

a first lid provided at the first end of the housing and comprising a first fluid port, a first compartment, a second compartment and a first internal separating wall separating the first compartment from the second compartment;

a second lid provided at the second end of the housing and comprising a second fluid port, a third fluid port, a third compartment, a fourth compartment and a second internal separating wall separating the third compartment from the fourth compartment;

a plurality of hollow fibers arranged within the housing, wherein each of the plurality of hollow fibers comprises a semi-permeable membrane and defines a fluid channel extending longitudinally through an interior of the respective hollow fiber;

a first sealing means which separates the fluid chamber from the first and the second compartment, the first sealing means having a first longitudinal end facing away from the second lid;

a second sealing means which separates the fluid chamber from the third and the fourth compartment, the second sealing means having a second longitudinal end facing away from the first lid;

a fourth fluid port and a fifth fluid port both provided at the fluid chamber and located between the first longitudinal end of the first sealing means and the second longitudinal end of the second sealing means;

wherein the first fluid port is arranged at the first compartment, wherein the second fluid port is arranged at the third compartment, wherein the third fluid port is arranged at the fourth compartment, wherein the plurality of hollow fibers comprises a first group of fibers and a second group of fibers, wherein each hollow fiber of the first group of fibers extends from the first compartment through the fluid chamber to the third compartment and, for directing a first fluid, fluidly connects the first compartment with the third compartment via the fluid channels extending through the interior of each hollow fiber of the first group of fibers, and wherein each hollow fiber of the second group of fibers extends from the second compartment through the fluid chamber to the fourth compartment and, for directing a second fluid, fluidly connects the second compartment with the fourth compartment via the fluid channels extending through the interior of each hollow fiber of the second group of fibers, and wherein the fourth and the fifth fluid port are fluidly connected to one another and both in fluidic communication with an exterior of both the hollow fibers of the first and the second group of fibers via the fluid chamber, wherein the system further comprises a line for draining the first fluid from the second fluid port of the filter device;

and wherein the system further comprises a substitution fluid line for draining the second fluid from the fourth compartment, the substitution fluid line, at a connection site, being fluidly connected to the line for diluting or mixing the first with the second fluid, wherein the line and the substitution line are being arranged outside the housing of the filter device, and wherein the line comprises a flow reducing means, the flow reducing means being positioned between the second fluid port and connection site.

With this embodiment, a post dilution can be achieved, and the substitution fluid flow is controlled by the flow reducer in the extracorporeal circuit, i.e. in the line, which is located after the filter device and before the entry point, i.e. connection site, of the substitution fluid line.

The flow reducing means reduce the flow of the first fluid through the line, thereby creating a relative pressure difference between the fourth fluid port and the third fluid port (the substitution fluid line), causing the second fluid, which is present in the fluid chamber, to enter the semi-permeable membranes and the fluid channels extending though the interior of the hollow fibers of the second group of fibers, and subsequently, to enter the fourth compartment in the second lid. Via the fourth compartment, and still necessitated by the pressure difference caused by the flow reducing means, the second fluid, or rather a part of the second fluid, is draining from the third fluid port into the substitution fluid line, thus diluting the first fluid guided within the line.

Accordingly, the installation of a pump actively draining the second fluid from the fourth compartment into the substitution line is not needed.

Also, with the embodiment described above, the substitution line is fluidly connecting the third fluid port to the second fluid port of the filter device.

It is to be understood that a flow reducing means can be any means suitable for reducing the flow of a first fluid through a line that otherwise, i.e. without the flow reducing means, would flow in a non-reduced manner through the line.

According to an alternative embodiment of the system according to the first aspect of the present invention, instead of a first lid comprising a first and a second compartment, a lid with only one compartment can be provided, wherein also each hollow fiber of the second group of fibers, extending from the second compartment through the fluid chamber to the fourth compartment, comprises a closed end in the first lid, such, that, for directing a second fluid, the second fluid is directed into fluid channels extending through the interior of each hollow fiber of the second group of fibers and directed into the fourth compartment, without providing a fluid connection between the second compartment and the fourth compartment.

Also, and according to a preferred embodiment of the first aspect, the flow reducing means can be controllable or non-controllable. Hereby, "controllable" is meant to be understood as a flow reducing means being operable, either manually, mechanically or electronically, such, that the fluid flow, during operation, can be actively controlled, e.g. to a stronger or lesser extend via the flow reducer. In this connection, "non-controllable" is meant to be understood as a mechanic means, e.g. a clamp-like device or a neck piece mounted in/onto the line, thereby mechanically, i.e. via a reduced diameter of the line at this site, reducing the fluid flow in the line.

According to second aspect, the present invention relates to a system for filtration of fluids, comprising a filter device for filtration of fluids, wherein said filter device comprises:

a housing having a first end and a second end and defining a fluid chamber extending between the first end and the second end;

a first lid provided at the first end of the housing and comprising a first fluid port, a first compartment, a second compartment and a first internal separating wall separating the first compartment from the second compartment;

a second lid provided at the second end of the housing and comprising a second fluid port and a second lid compartment, the second lid compartment representing a single compartment not being separated by internal separating means;

a plurality of hollow fibers arranged within the housing, wherein each of the plurality of hollow fibers comprises a semi-permeable membrane and defines a fluid channel extending longitudinally through an interior of the respective hollow fiber;

a first sealing means which separates the fluid chamber from the first and the second compartment, the first sealing means having a first longitudinal end facing away from the second lid;

a second sealing means which separates the fluid chamber from the second lid compartment, the second sealing means having a second longitudinal end facing away from the first lid;

a fourth fluid port and a fifth fluid port both provided at the fluid chamber and located between the first longitudinal end of the first sealing means and the second longitudinal end of the second sealing means;

wherein the first fluid port is arranged at the first compartment, wherein the second fluid port is arranged at the second lid compartment, wherein the plurality of hollow fibers comprises a first group of fibers and a second group of fibers, wherein each hollow fiber of the first group of fibers extends from the first compartment through the fluid chamber to the second lid compartment and, for directing a first fluid, fluidly connects the first compartment with the second lid compartment via the fluid channels extending through the interior of each hollow fiber of the first group of fibers, and wherein each hollow fiber of the second group of fibers extends from the second compartment through the fluid chamber to the second lid compartment and, for directing a second fluid, fluidly connects the second compartment with the second lid compartment via the fluid channels extending through the interior of each hollow fiber of the second group of fibers, and wherein the fourth and the fifth fluid port are fluidly connected to one another and both in fluidic communication with an exterior of both the hollow fibers of the first and the second group of fibers via the fluid chamber.

With this embodiment, within the filter device, or rather within the second lid compartment, a dilution or mixing of the first fluid, that is directed to the second lid compartment with the second fluid, that is also directed to the second lid compartment, can be directly achieved, without the need of externally, i.e. external of the filter device, diluting the first fluid with the second fluid.

According to a third aspect, a system for filtration of fluids is provided, comprising a filter device for filtration of fluids, wherein said filter device comprises:

a housing having a first end and a second end and defining a fluid chamber extending between the first end and the second end;

a first lid provided at the first end of the housing and comprising a first fluid port and a first compartment, the first compartment being a single compartment and not being separated by internal separating means;

a second lid provided at the second end of the housing and comprising a second fluid port and a second lid compartment;

a plurality of hollow fibers arranged within the housing, wherein each of the plurality of hollow fibers comprises a semi-permeable membrane and defines a fluid channel extending longitudinally through an interior of the respective hollow fiber;

a first sealing means which separates the fluid chamber from the first compartment, the first sealing means having a first longitudinal end facing away from the second lid;

a second sealing means which separates the fluid chamber from the second lid compartment, the second sealing means having a second longitudinal end facing away from the first lid;

a third fluid port and a fourth fluid port both provided at the fluid chamber and located between the first longitudinal end of the first sealing means and the second longitudinal end of the second sealing means;

wherein the first fluid port is arranged at the first compartment, wherein the second fluid port is arranged at the second lid compartment, wherein the plurality of hollow fibers comprises a first group of fibers and a second group of fibers, with each hollow fiber of the first and the second group of fibers comprising a first end and a second end, wherein each hollow fiber of the first group of fibers extends via its respective first end from the first compartment through the fluid chamber to, via its second end, the second lid compartment, and, for directing a first fluid, fluidly connects the first compartment with the second lid compartment via the fluid channels extending through the interior of each hollow fiber of the first group of fibers, and wherein each hollow fiber of the second group of fibers substantially extends, via its respective first end, from the first compartment through the fluid chamber to, via its respective second end, the second lid compartment, wherein each hollow fiber of the second group of fibers at its respective first end is closed, so that there is no fluid connection between the first compartment with the second lid compartment, with the fluid channels extending from the closed first end through the interior of each hollow fiber of the second group of fibers to the second lid compartment, and wherein the fourth and the fifth fluid port are fluidly connected to one another and both in fluidic communication with an exterior of both the hollow fibers of the first and the second group of fibers via the fluid chamber.

With this embodiment, in particular with the provision that each hollow fiber of the second group of fibers at its respective first end is closed, and with the provision that the fluid channels extend from the closed first end through the interior of each hollow fiber of the second group of fibers to the second lid compartment, a second fluid, present in the fluid chamber, can be directed through said fluid channels extending through the interior of each hollow fiber of the second group of fibers to the second lid compartment for dilution/mixing with the first fluid in the second lid compartment. In that way, the necessity of providing an external dilution, i.e. a dilution outside the filter device, can be prevented.

Within the present invention, the expression "substantially" in respect of each hollow fiber of the second group of fibers "substantially" extending, is meant to comprise any— i.e. to the most part—fiber that is extending from the first compartment through the fluid chamber to the second lid compartment—and has its first end closed —, as well as any fiber that might be slightly shorter, and that, accordingly, terminates, via their first end, in the first sealing means, whereby the first end is closed.

In a still further aspect of the present invention, a method for filtration and/or dilution of fluids using the aforementioned filter device and/or system is presented, the method comprising the steps of:

introducing a first fluid into the filter device through the first fluid port;

directing the first fluid from the first lid to the second lid via the first compartment, the fluid channels in the interior of the first group of hollow fibers and to the third compartment;

draining the first fluid from the filter device through the second fluid port via line;

introducing a second fluid into the filter device through the fourth fluid port;

draining a first part of the second fluid from the filter device through the fifth fluid port;

filtering a second part of the second fluid by guiding it from the fourth fluid port via the fluid chamber to the exterior of the second group of hollow fibers, through the semipermeable membranes of the second group of hollow fibers into the fluid channels in the interior of the second group of hollow fibers and to the third fluid port;

draining the filtered second part of the second fluid from the filter device through the third fluid port via substitution fluid line; and, diluting the filtered first fluid with the filtered second part of the second fluid by fluidly connecting the substitution fluid line with the line.

The described method can be performed with the system according to the first aspect of the present invention.

According to another aspect of the invention, a method for filtration and/or dilution of fluids using the aforementioned filter device and/or system is presented, the method comprising the steps of:

introducing a first fluid into the filter device through the first fluid port;

directing the first fluid from the first lid to the second lid via the first compartment and the fluid channels in the interior of the first group of hollow fibers into the second lid compartment;

introducing a second fluid into the filter device through the fourth fluid port;

draining a first part of the second fluid from the filter device through the fifth fluid port;

filtering a second part of the second fluid by guiding it from the fourth fluid port via the fluid chamber to the exterior of the second group of hollow fibers, through the semipermeable membranes of the second group of hollow fibers into the fluid channels in the interior of the second group of hollow fibers and into the second lid compartment, thereby diluting the first fluid with the second fluid; and optionally draining the diluted mixture of the first and the second fluid from the filter device through the second fluid port.

Preferred embodiments of the invention are defined in the dependent claims. It shall be understood that the claimed systems and methods to be described have similar and/or identical preferred embodiment as the claimed filter device and as defined in the dependent claims.

Also, it is noted that the following description regarding parts and features of the systems according to the invention, that are shared by the three aspects of the invention as detailed above, applies for each of the three aspects and methods, i.e. the first, second and third aspect of the system and the two methods according to the invention.

Accordingly, the first fluid port and the second fluid port are configured to introduce a first fluid from the exterior into the filter device and to remove the introduced first fluid after filtration. For instance, the first fluid port functions as a fluid inlet, whereas the second fluid port functions as a fluid outlet.

Subsequently, the introduced first fluid reaches the first compartment that is in direct fluid connection to the first fluid port. The first fluid then enters the internal fluid channel of the first group of hollow fibers and may flow across the fluid chamber before arriving at the second lid. After reaching the third compartment of the second lid in case of the first aspect of the invention, or after reaching the second lid compartment in case of the second and third aspect of the invention, which third compartment/second lid compartment is in direct fluid connection to the second open end of the first group of hollow fibers as well as to the second fluid port, the first fluid may be removed from the filter device through the second fluid port.

Further, a second fluid may be introduced into the filter device through the fourth fluid port and, after flowing inside the fluid chamber, removed from the filter device through the fifth fluid port. The fourth fluid port may be arranged closer to the second end of the filter device than the fifth fluid port.

In case where the first lid comprises a first and a second compartment, since the first compartment is separated from the second compartment of the first lid, no fluid can flow between the first and second compartment. For the same reason, and in case the second lid comprises a third and a fourth compartment, no fluid can flow between the third and fourth compartment of the second lid.

The first sealing means defines a longitudinal end of either the first and second compartment facing the fluid chamber (in case of the first and second aspect of the system according to the invention), or a longitudinal end of the single first compartment (in case of the third aspect of the system according to the invention). The second sealing means defines a longitudinal end of the third and fourth compartment facing the fluid chamber (in case of the first aspect of the system according to the invention), or of the second lid compartment in case of the second and third aspect of the system according to the invention. The first and second group of hollow fibers are connected to the first and second lid via the first and second sealing means, respectively. The first and second sealing means are preferably configured to achieve a sealing effect such that only fluids flowing along and inside the internal fluid channels of the first and second group of hollow fibers may enter the respective compartments of the first and second lid coming from the central fluid chamber. In other words, no fluid may directly enter from the central fluid chamber or the respective compartments of the first and second lid through the sealing means.

Dialysis-type treatments can therefore be performed using the systems according to the present invention. In this case, blood from a patient, which is introduced into the filter device at the first fluid port as the first fluid, wherein a dialysis fluid is introduced into the filter device at the fourth fluid port as the second fluid mentioned above.

Accordingly, and according to a preferred embodiment of the aspects of the system and methods according to the invention, the first fluid is blood of a patient, preferably of a human patient, and the second fluid is a dialysis and/or substitution fluid.

In this way, blood introduced into the filter device via the first fluid port enters the first compartment of the first lid, then flows through the internal fluid channels of the first group of hollow fibers to the third compartment of the second lid in case of the first aspect of the system and method according to the present invention, or to the second lid compartment in case of the second and third aspect of the system and method according to the invention, such that it may finally exit the filter device via the second fluid port. Since the hollow fibers of the first group comprise each a semi-permeable wall, various convection and diffusion processes may take place across these semi-permeable membranes. Such processes serve to purify and replenish the blood and to remove excess fluid from the blood.

The expression "the fourth and fifth fluid port are in fluidic communication via the fluid chamber to the exterior of the plurality of hollow fibers" means that a fluid entering the fourth or the fifth fluid port may reach the exterior of the plurality of hollow fibers via the fluid chamber. In particular, since the fourth and fifth fluid port are in fluidic communication via the fluid chamber to the exterior/outside of each of the first group of hollow fibers, the dialysis fluid introduced into the fluid chamber, e.g. through the fourth fluid port, can reach the outer surface of the semi-permeable membranes of the first group of hollow fibers. This facilitates removal of excess fluid and diffusion of waste products from the internal fluid channels of the first group of hollow fibers through the semipermeable membranes into the space within the fluid chamber outside of the first group of hollow fibers. The excess fluid and waste products can be removed from the fluid chamber, e.g. through the fifth fluid port, together with the dialysis fluid.

According to all aspects of the present invention, the second fluid, e.g. the substitution fluid, which may e.g. comprise water, is added post the filtration unit.

During haemodiafiltration a certain amount of plasma water is removed from the patient's blood. This lack of plasma water needs to be replaced. The herein presented device allows for replacing the plasma water based on a filtration of dialysis fluid. The dialysis fluid is introduced through the fourth fluid port into the filter device. Since the fourth and the fifth fluid port are both fluidly connected not only to the exterior/outside of each of the first group of hollow fibers, but also to the exterior/outside of each of the second group of hollow fibers via the fluid chamber, the useful substances contained in the introduced dialysis fluid may permeate the internal fluid channels of the second group of hollow fibers through the semi-permeable membranes (from the outside to the inside of the hollow fibers) such that the dialysis fluid is thereby filtered. This filtered dialysis fluid including the useful/essential substances can then be used as substitution fluid that replaces the plasma water extracted from the patient during haemodiafiltration. It may enter the fourth compartment of the second lid in case of the first aspect of the system according to the invention, and exit the filter device through the third fluid port, which is in direct fluid connection with the line draining the first fluid, i.e. blood, from the filter device. In case of the second and third aspect of the system according to the invention, the substitution fluid enters the second lid compartment, where it directly mixes with the first fluid present in the second lid compartment, e.g. filtered blood, thereby diluting/replenishing the blood with water.

In this way, the filter device according to the present invention serves as a filter for producing, purifying, and/or filtering useful fluids, e.g. substitution fluids, infusion fluids and/or buffer fluids, based on the second fluid, e.g. the dialysis fluid. Advantageously, producing substitution fluids is possible even without providing an additional filter, since the filter device that is also used for filtering the first fluid, e.g. blood, already fulfills the function of such an additional filter, i.e. to filter the useful/essential fluids from the second fluid, e.g. the dialysis fluid.

The present invention is also advantageous since producing, purifying and/or filtering the useful fluids based on the second fluid is possible without providing a wall inside the fluid chamber to separate the first group of hollow fibers from the second group of hollow fibers. Whilst such a wall may generally be provided in the present invention, it is not necessary to do so in the present invention in order to produce and/or to purify the useful fluids.

The fluid chamber of the systems according to the aspects of the present invention is preferably formed as a single-compartment-chamber to accommodate both the first and second group of hollow fibers without a wall in between them. Also, the second fluid introduced through the fourth fluid port can reach both the first and the second group of hollow fibers before exiting the filter device through the fifth fluid port.

In a preferable embodiment, the fourth and the fifth fluid port are in direct fluid connection to the fluid chamber, the direct fluid connection being located between the first longitudinal ends of the first sealing means and the second longitudinal ends of the second sealing means.

In this way, the openings of the fourth and fifth fluid port, through which fluid may flow directly between the respective fluid port and the fluid chamber, are located within the first longitudinal end of the first sealing means and the second longitudinal end of the second sealing means.

This ensures that fluids that are introduced into the fluid chamber through the fourth and/or fifth fluid port are not able to flow into the compartment(s) of the first lid or the compartment(s) of the second lid. The afore-mentioned openings of the fourth and the fifth fluid ports are preferably arranged to extend beyond a longitudinal end of the first and second sealing means facing the fluid chamber in the longitudinal direction.

In another preferable embodiment, the fluid chamber is spatially confined by an inner, tubular wall of the housing, the first sealing means and the second sealing means.

In this way, the fluid chamber is confined circumferentially by the inner tubular wall of the housing, wherein the fluid chamber is confined longitudinally by the first sealing means and the second sealing means, in particular by the longitudinal ends of the first and second sealing means facing towards the fluid chamber.

In another preferable embodiment of the systems according to the first and second aspects of the present invention, the first compartment is fluidly isolated from the second compartment by means of the first sealing means and the first internal separating wall. Also, in another preferable embodiment of the first aspect of the system and method according to the invention, the third compartment is fluidly isolated from the fourth compartment by means of the second sealing means and the second internal separating wall.

In another preferred embodiment, the first and/or the second sealing means of the systems of all aspects of the invention comprises a potting compound for receiving the first and/or the second group of hollow fibers.

Potting compounds are advantageous for both providing an anchoring means to secure the hollow fibers and/or sealing the compartment(s) of the respective lid against the fluid chamber.

In another preferable embodiment according to the first and second aspect of the system and method according to the present invention, the filter device further comprises a sixth fluid port arranged at the second compartment of the first lid, the sixth fluid port being closed by a closing means.

In this way, the filter device can be build symmetrically with respect to a middle surface perpendicular to the longitudinal direction of the housing. This enables to use the different fluid ports at both ends of the housing as fluid inlet or outlet.

In another preferred embodiment of all aspects of the system and method according to the present invention, the first group of hollow fibers comprises more fibers than the second group of hollow fibers. According to exemplary embodiments, the first group of hollow fibers may comprise at least 70%, at least 80%, or at least 90% of the hollow fibers arranged within the filter device.

In this way, the filtration rate is increased by directing the first fluid through the first group of hollow fibers. In particular, the dialysis-type treatments are more efficient.

In another preferred embodiment of all aspects of the system and method according to the present invention, the fluid chamber has at least a part having a circular-cylindrical shape.

This is advantageous regarding a symmetric design of the filter device so that it can be used to direct fluids in either direction along the fluid chamber. Further, a cylindrical shaped fluid chamber is relatively easy to form compared to irregularly shaped chambers.

The system and method according to all aspects of the present invention is advantageous for filtering the second fluid introduced into the filter device through the fourth or the fifth fluid port and thereby produce a substitution fluid from the filtered second fluid, wherein said substitution fluid can be added to the treated blood of the patient to compensate for the typical removal of plasma water from the patient's blood that occurs during haemodiafiltration. Thus, no extra/additional source of substitution fluid needs to be provided, since the system according to all aspects of the present invention enables to filter the dialysis fluid to produce substitution fluid.

In a preferable embodiment, the system and method according to all aspects of the present invention further comprises: (i) an arterial line for fluidly connecting an arterial side of a patient access to the first fluid port of the filter device, (ii) a venous line for fluidly connecting a venous side of the patient access to the second fluid port of the filter device, (iii) a first pump for pumping a first fluid into the first fluid port and/or for draining the first fluid from the second fluid port of the filter device, and (iv) a second pump for pumping a second fluid into the fourth fluid port and/or for draining the second fluid from the fifth fluid port of the filter device.

The system advantageously enables the type of treatment, in which blood is taken from an arterial side of a patient access and given to a venous side of the patient access after filtration and/or dilution by the filter device. Further, the flow of the second fluid, in particular dialysis fluid, is assisted by the second pump.

In another preferred embodiment of the first aspect of the system and method according to the invention, the substitution fluid line is—via the connection site with the line— fluidly connected to the venous line, thus rendering the use of the filter device in a post-dilution mode.

In another preferred embodiment, the systems and methods of all aspects of the present invention further comprise a further line for fluidly connecting the second fluid port of the filter device to a waste handling unit and/or a waste bag.

In this way, the system can be used to perform priming and/or rinseback of the filter device, wherein waste fluid removed from the filter device can be selected and/or further processed in a secure way, thereby advantageously minimizing impacts to the environment.

BRIEF DESCRIPTION OF THE DRAWINGS

These and other aspects of the invention will be apparent from and elucidated with reference to the embodiments described hereinafter. In the following drawings.

DETAILED DESCRIPTION OF THE INVENTION

Figure 9:
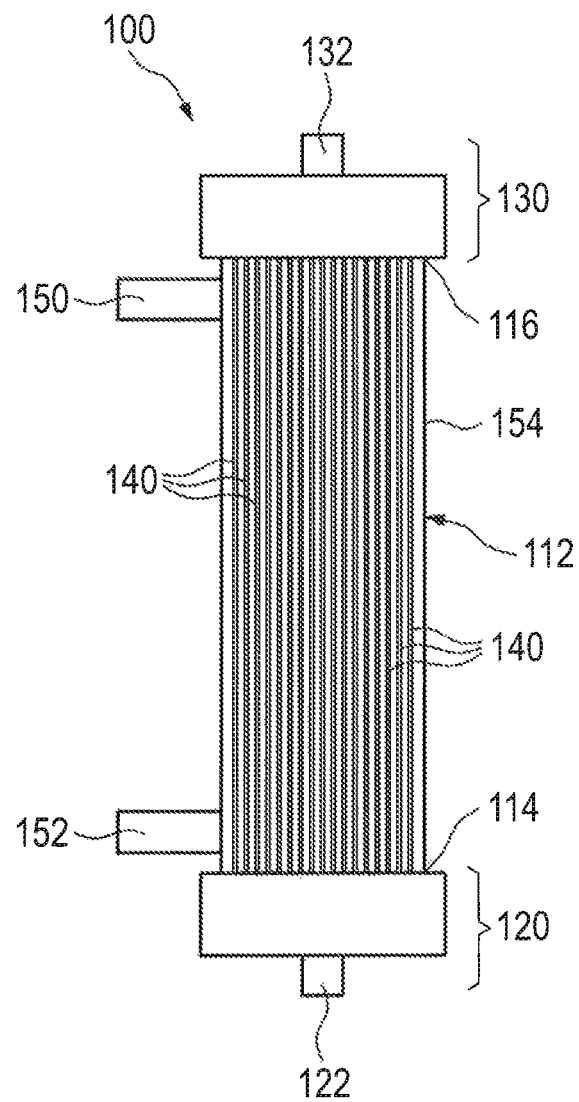
FIG. 9 schematically shows a filter device according to the prior art.

A filter device 100 for filtration of fluids, in particular for dialysis-type treatments generally known from the prior art is schematically shown in FIG. 9. The filter device 100 comprises a housing 112 and two end-caps 120, 130. The housing 112 comprises a longitudinally extending tubular wall 154 having two opposed ends 114, 116, wherein the end-caps 120, 130 are arranged each at one of both ends 114, 116. A fluid port 122, 132 is provided at each of the two end-caps 120, 130 for introducing blood from a patient and removing the blood after being filtered. Two additional fluid ports 150, 152 are arranged each at one of the two ends 114, 116. The two additional fluid ports 150, 152 are used for introducing and removing a dialysis fluid. A plurality of hollow fibers 140 are arranged within a chamber of the housing 112 for directing the introduced blood from one end-cap 120 to the other end-cap 130.

Figure 1:
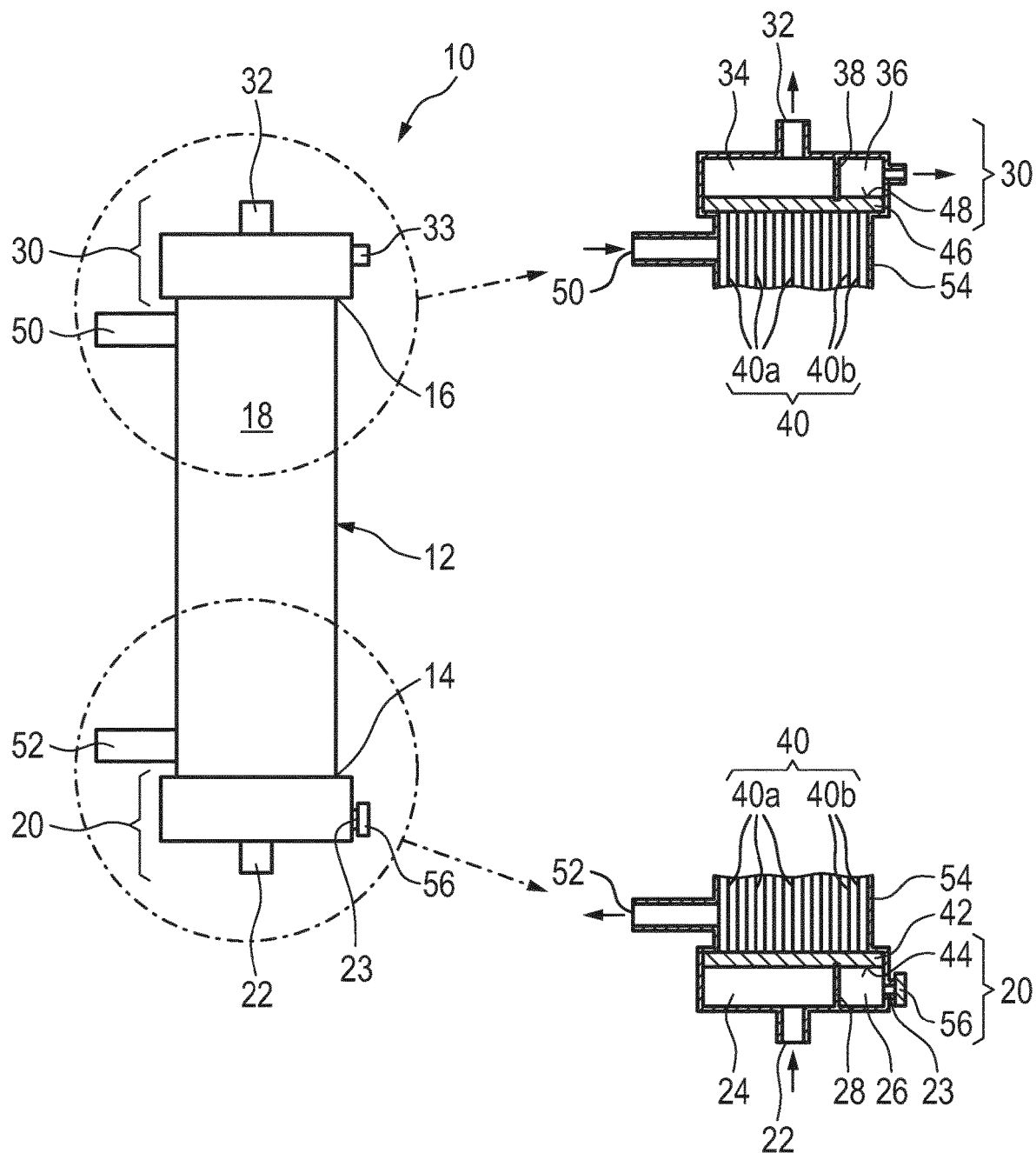
FIG. 1 schematically shows a filter device according to a general embodiment.

FIG. 1 shows an embodiment of a filter device 10 which may be used for treating blood (as in a "regular" dialyser) and for (additionally) filtering dialysis fluid.

Figure 4:
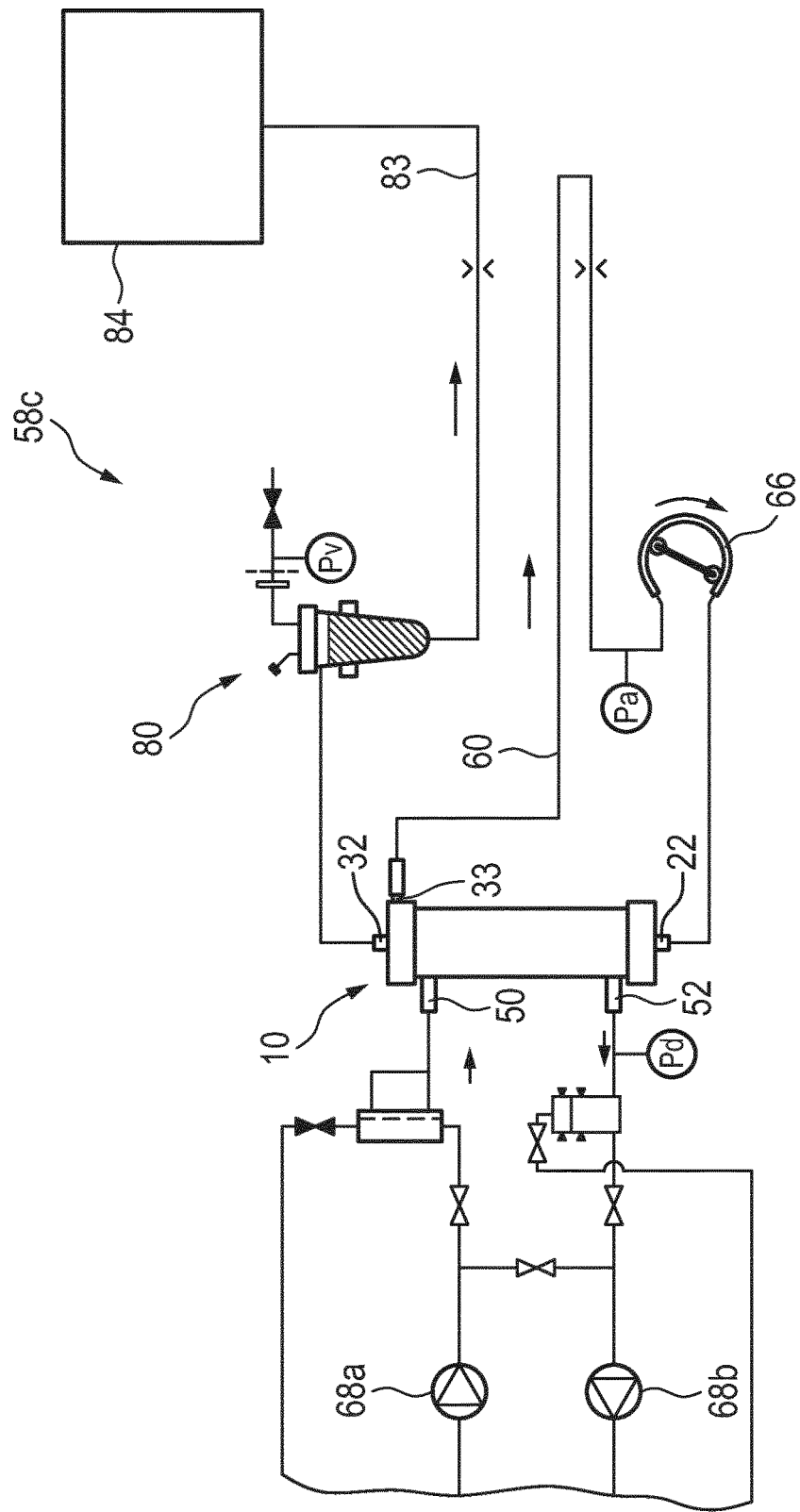
FIG. 4 schematically shows a system according to further embodiment.
Figure 5:
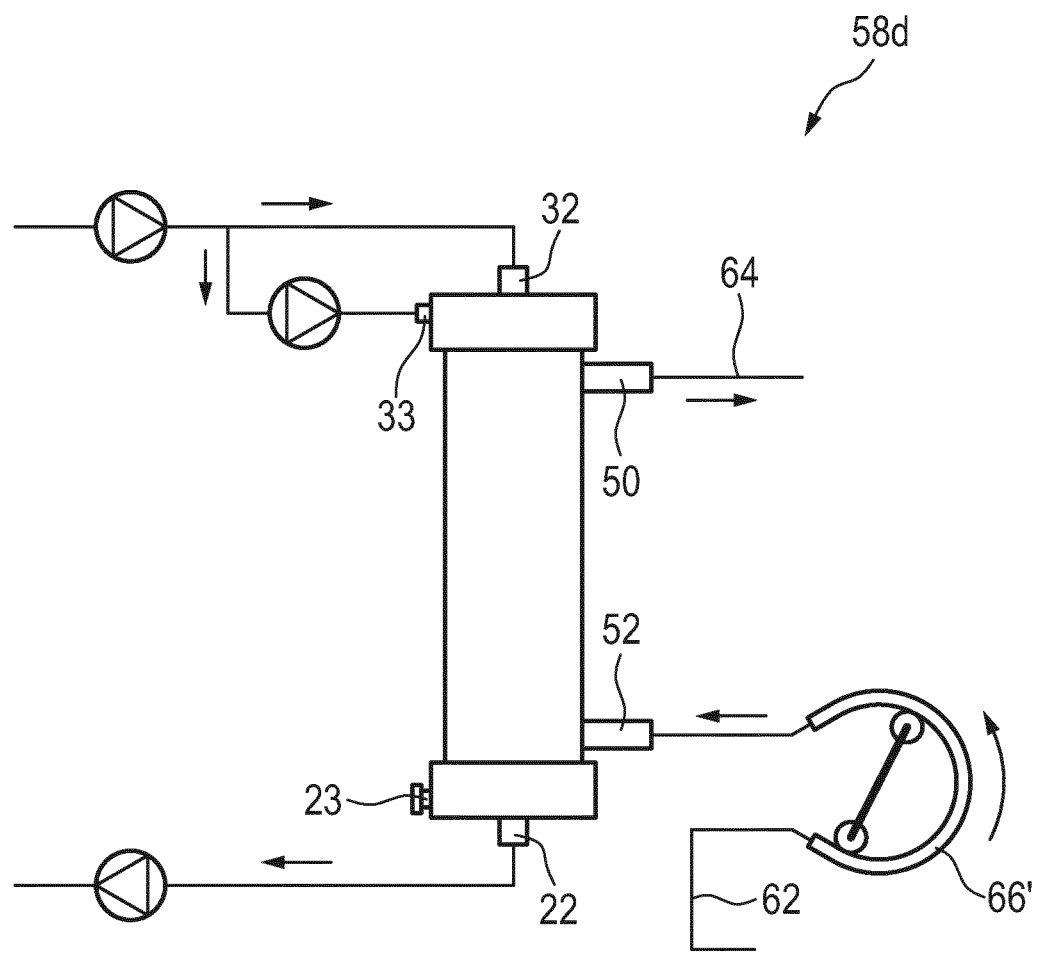
FIG. 5 schematically shows a system according to a still further embodiment.
Figure 6:
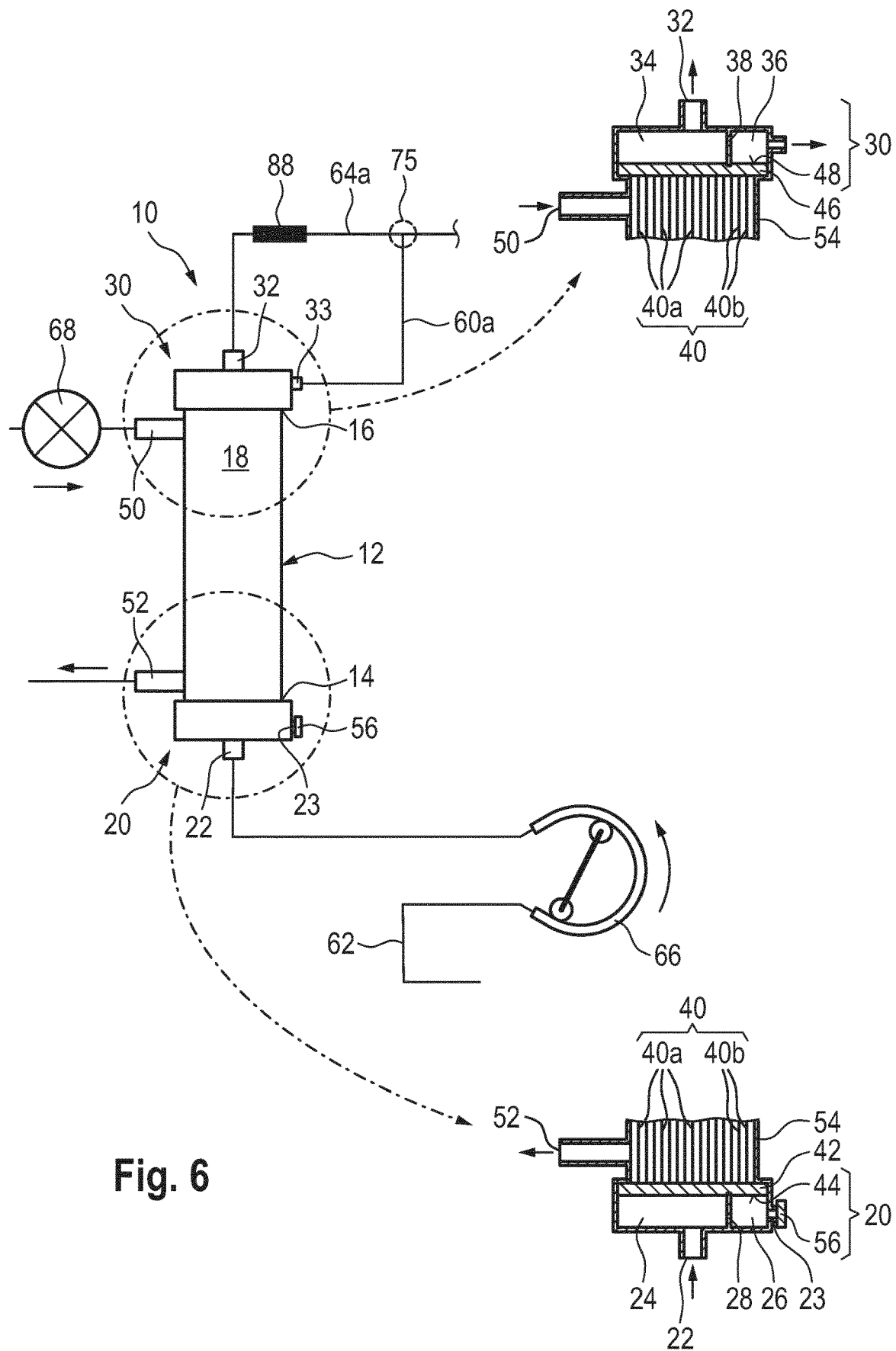
FIG. 6 schematically shows a first aspect of the system according to the present invention.
Figure 7:
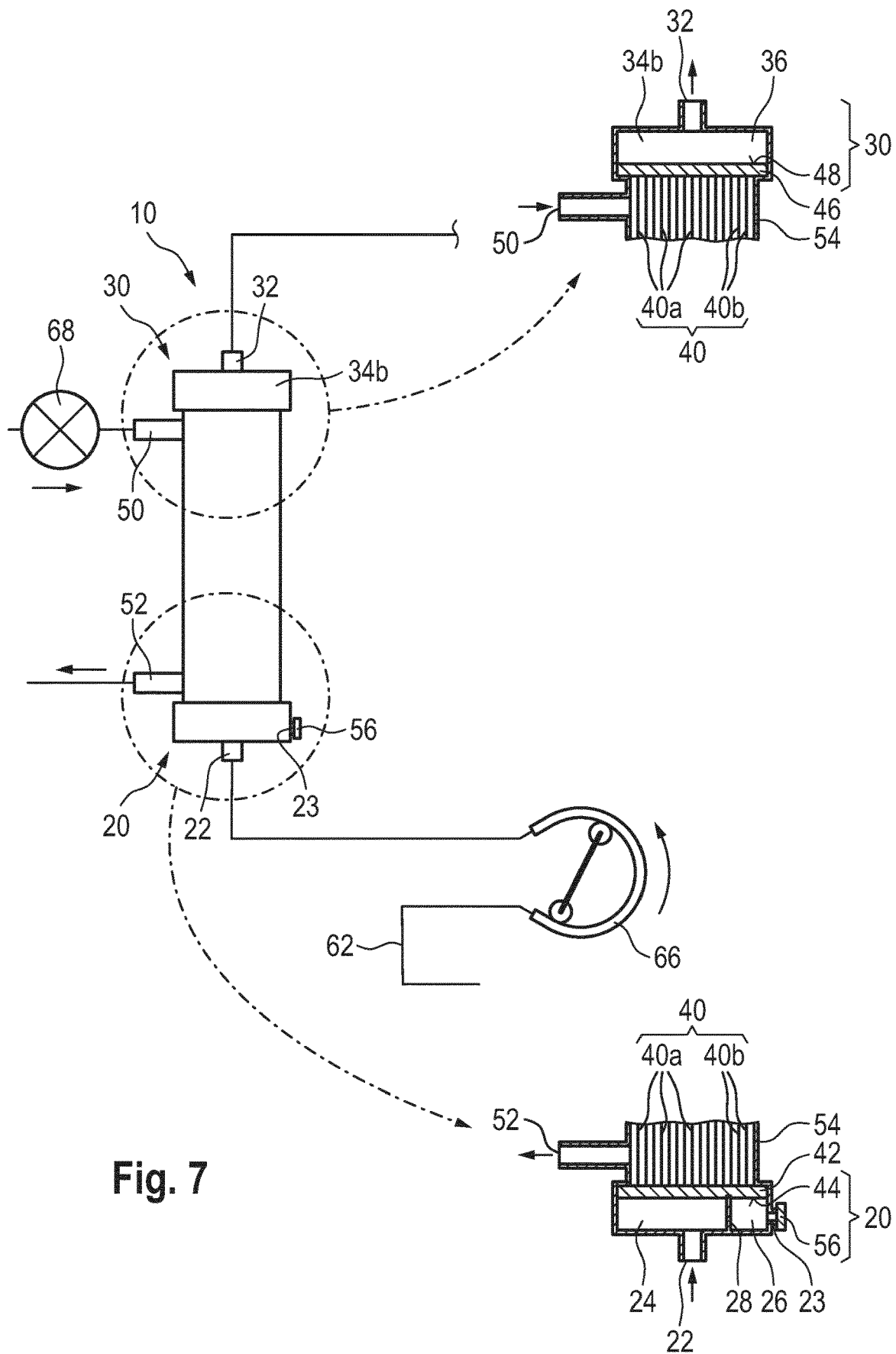
FIG. 7. schematically shows a system according to second aspect of the present invention.
Figure 8:
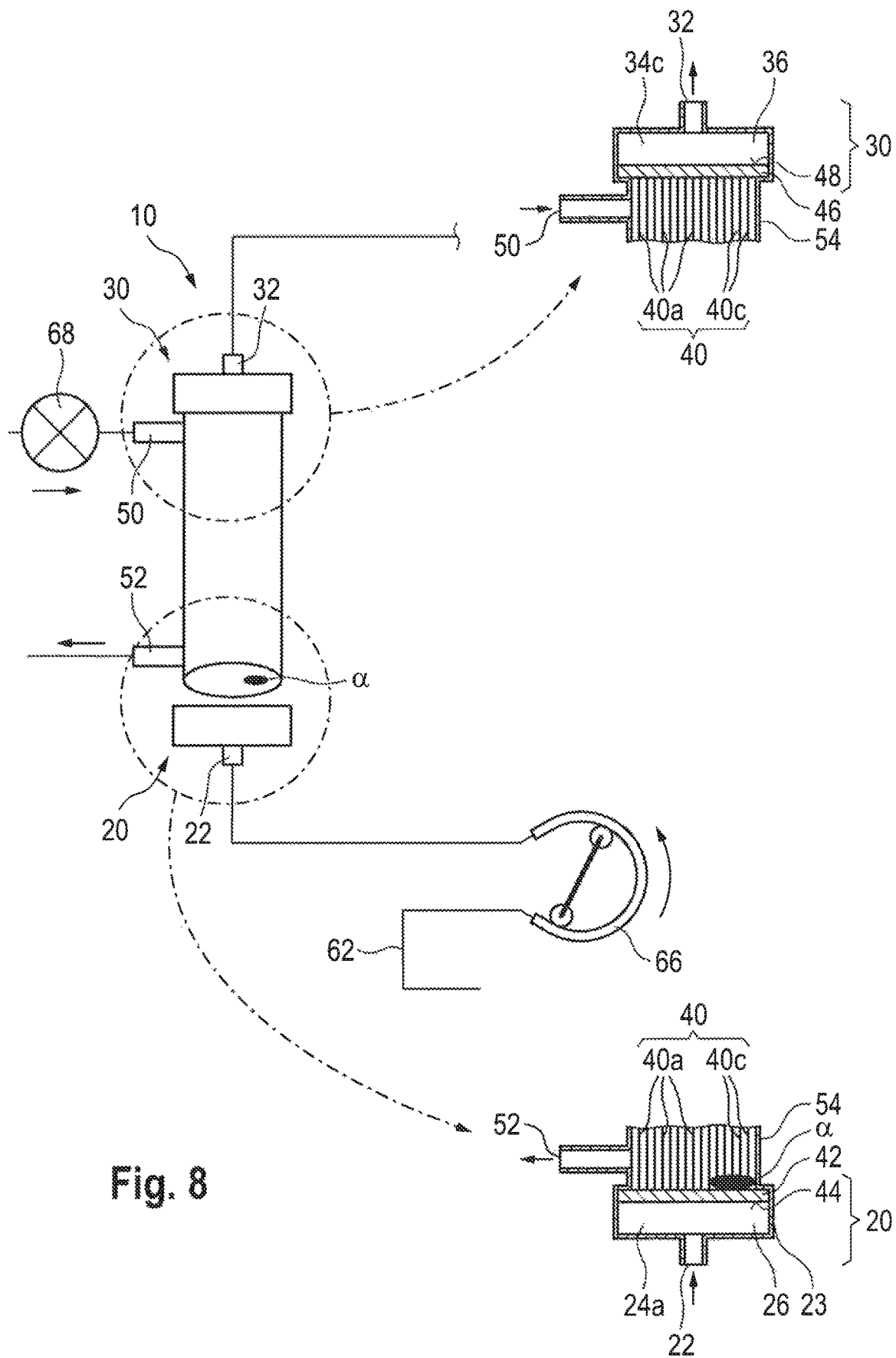
FIG. 8 schematically shows a system according to a third aspect of the present invention.

By means of the filter device and systems shown in FIGS. 1 to 5, the features of the aspects of the systems according to the present invention, as detailed in FIGS. 6 to 8, and as far as shared with the filter and systems as shown in FIGS. 1 to 5, will be exemplarily explained and described in detail.

In other words, the following description and disclosure of features, which are the same for the systems and devices of different embodiments and for the aspects of the present invention, shall be effectively made for every embodiment/ aspect.

The filter device 10 comprises a housing 12 having a first end 14 and a second end 16 and defines a fluid chamber 18 extending between the first end 14 and the second end 16. As shown in the FIGS. 1 to 8, the fluid chamber 18 preferably has a substantially circular-cylindrical shape.

As shown in FIGS. 1 to 8, a first lid 20 is provided at the first end 14 of the housing 12 and comprises a first fluid port 22, a first compartment 24, a second compartment 26 and an internal separating wall 28 separating the first compartment 24 from the second compartment 26. Similarly, a second lid 30 is provided at the second end 16 of the housing 12 and comprises a second fluid port 32, a third compartment 34, a fourth compartment 36 and an internal separating wall 38 separating the third compartment 34 from the fourth compartment 36.

A plurality of hollow fibers 40 are arranged within the housing 12, each of the fibers 40 defining an internal fluid channel extending longitudinally through an interior of the respective hollow fiber. Each fiber comprises a semi-permeable membrane which sidely confines the respective internal fluid channel. The semi-permeable membrane is preferably configured to allow substances, whose size is below a threshold size, to enter the internal fluid channel from exterior of the fiber and/or to exit the internal fluid channel to the exterior of the fiber.

A first sealing means 42 is provided at the first end 14 of the housing 12 for separating the fluid chamber 18 from the first and the second compartment 24, 26. The first sealing means 42 has a first longitudinal end 44 facing away from the second lid 30. Further, a second sealing means 46 is provided at the second end 16 for separating the fluid chamber 18 from the third and the fourth compartment 34, 36, the second sealing means 46 having a second longitudinal end 48 facing away from the first lid 20.

The filter device 10 further comprises a fourth fluid port 50 and a fifth fluid port 52, both being provided at the fluid chamber 18 and located between the first longitudinal end 44 of the first sealing means 42 and the second longitudinal end 48 of the second sealing means 46.

The first fluid port 22 is arranged at the first compartment 24, thereby allowing a direct fluid connection to the first compartment 24. The second fluid port 32 is arranged at the third compartment 34, thereby allowing a direct fluid connection to the third compartment 34. The third fluid port 33 is arranged at the fourth compartment 36, thereby allowing a direct fluid connection to the fourth compartment 36.

The plurality of hollow fibers 40 comprise a first group of fibers 40a and a second group of fibers 40b. Each hollow fiber of the first group 40a extends from the first compartment 24 through the fluid chamber 18 to the third compartment 34, wherein each hollow fiber of the second group 40b extends from the second compartment 26 through the fluid chamber 18 to the fourth compartment 36.

The first and second group of hollow fibers 40a, 40b extend each from a first open end to a second open end. The first open ends are each received by the first sealing means 42. The second open ends are each received at the second sealing means 46. The first and second sealing means 42, 46 are here each provided as a potting compound, into which the fibers 40a, 40b extend. In FIGS. 1 to 8, it is shown that the two sealing means 42, 46 are arranged within the first and second lid 20, 30, respectively. This is, however, only exemplary. In general, at least one of the two sealing means 42, 46 may be arranged outside of the respective lid towards the center of the housing 18.

The first compartment 24 is in direct fluid connection to the internal fluid channels of the first group of hollow fibers 40a at their first open ends. The third compartment 34 is in direct fluid connection to the internal fluid channels of the first group of hollow fibers 40a at their second open ends. Similarly, the second compartment 26 is in direct fluid connection to the internal fluid channels of the second group of hollow fibers 40b at their first open ends. The fourth compartment 36 is in direct fluid connection to the internal fluid channels of the second group of hollow fibers 40b at their second open ends.

The fourth and the fifth fluid port 50, 52 are fluidly connected to one another and in fluid communication with the exterior side of the plurality of hollow fibers 40 via the fluid chamber 18. This means that a fluid that is introduced to one of the fourth and the fifth fluid port 50, 52 is able to reach the other of these two fluid ports via the fluid chamber 18. Also, a fluid that is introduced to one of these two fluid ports is able to reach the outer surface of the semi-permeable membranes of the both the first group and the second group 40a, 40b of hollow fibers.

The first fluid port 22 and the second fluid port 32 are configured for introducing a first fluid from the exterior into the filter device 10 and for removing the introduced first fluid after filtration. Preferably, the first fluid port 22 functions as a fluid inlet, wherein the second fluid port 32 functions as a fluid outlet.

The introduced first fluid subsequently reaches the first compartment 24 that is in direct fluid connection to the first fluid port 22, as shown in FIGS. 1 to 6. The first fluid then enters the internal fluid channel of the first group of hollow fibers 40a and may flow across the fluid chamber 18 before arriving at the second lid 30. After reaching the third compartment 34 of the second lid 30, which is in direct fluid connection to the second open end of the first group of hollow fibers 40a as well as to the second fluid port 32, the first fluid may be removed from the filter device 10 through the second fluid port 32.

Further, a second fluid may be introduced into the filter device 10 through the fourth fluid port 50 and, after flowing inside the fluid chamber 18, removed from the filter device 10 through the fifth fluid port 52. The fourth fluid port 50 may be arranged closer to the second end 16 of the filter device 10 than the fifth fluid port 52.

Since the first compartment 24 is separated from the second compartment 26 of the first lid 20, no fluid can flow between the first and second compartment 24, 26. For the same reason, no fluid can flow between the third and fourth compartment 34, 36 of the second lid 30.

The first sealing means 42 defines a longitudinal end of the first and second compartment 24, 26 facing the fluid chamber 18. The second sealing means 46 defines a longitudinal end of the third and fourth compartment 34, 36 facing the fluid chamber 18. The first and second group of hollow fibers 40a, 40b are connected to the first and second lid 20, 30 via the first and second sealing means 42, 46, respectively.

Dialysis-type treatments can therefore be performed using the systems and methods according to the present invention. In this case, blood from a patient may be introduced into the systems as the first fluid, wherein a dialysis fluid may be introduced into the systems as the second fluid.

In this way, blood introduced through the first fluid port 22 flows in the internal fluid channels of the first group of hollow fibers 40a through the fluid chamber 18 of the filter device 10. Since the hollow fibers 40a of the first group comprise each a semipermeable membrane, various convection and diffusion processes may therefore take place across these semi-permeable membranes. Such processes serve to purify and replenish the blood and to remove excess fluids from the blood.

In particular, since the fourth and fifth fluid port 50, 52 are in fluidic communication with the first group of the hollow fibers 40a via the fluid chamber 18, the dialysis fluid (second fluid) introduced into the fluid chamber 18, e.g. through the fourth fluid port 50, can reach the outer surface of the semi-permeable membranes of the first group of hollow fibers 40a. This facilitates removal of excess fluid and diffusion of waste products from the internal fluid channels of the first group of hollow fibers 40a through their semi-permeable membranes into the exterior of these fibers 40a within the fluid chamber 18. The excess fluid and waste products can be removed from the fluid chamber 18, e.g. through the fifth fluid port 52, together with the dialysis fluid.

The blood that is to be introduced into the filter device 10 may be conditioned using a substitution fluid, an infusion fluid or a buffer (e.g. bicarbonate, acetate, etc.). The substances forming the substitution fluid, the infusion fluid or the buffer fluid contained in the introduced blood may therefore diffuse from within the internal fluid channels of the first group of hollow fibers 40a through the semi-permeable membrane into the exterior of these hollow fibers 40a and finally be removed from the filter device 10 through the fifth fluid port 52.

The second fluid (e.g. the dialysis fluid) is introduced through the fourth fluid port 50 into the filter device 10. Since the fourth and the fifth fluid port 50, 52 are both in fluidic communication with the second group of fibers 40b via the fluid chamber 18, the useful substances contained in the introduced second fluid may permeate into the internal fluid channels of the second group of hollow fibers 40b through the semi-permeable membranes of these fibers 40b such that the dialysis fluid is thereby filtered. This filtered dialysis fluid can then be used as substitution fluid that replaces the plasma water extracted from the patient during haemodiafiltration. It may enter the fourth compartment 36 of the second lid 30 and exit the filter device 10 through the third fluid port 33, which is in direct fluid connection to the fourth compartment 36.

In this way, the filter device 10 serves as a filter for producing useful fluids, e.g. substitution fluids, infusion fluids and/or buffer fluids, based on the second fluid, e.g. the dialysis fluid. Advantageously, producing substitution fluids is possible even without providing a wall inside the fluid chamber 18 to separate the first group of hollow fibers from the second group of hollow fibers. Without the presence of such a wall, the fluid chamber 18 is formed as a single-compartment-chamber to accommodate both the first and second group of hollow fibers 40a, 40b. Also, the second fluid introduced through the fourth fluid port 50 can reach both the first and second group of hollow fibers 40a, 40b before being removed from the filter device 10 through the fifth fluid port 52.

Preferably, the fourth and the fifth fluid port 50, 52 are in direct fluid connection to the fluid chamber 18, the direct fluid connection being located only between the first longitudinal end 44 of the first sealing means 42 and the second longitudinal end 48 of the second sealing means 46. In this way, the fourth and the fifth fluid port 50, 52 are fluidly separated from all the compartments 24, 26, 34, 36 at both lids 20, 30. More preferably, the fourth and fifth fluid port 50, 52 are arranged completely away from the first and second lid 20, 30 and/or from the first and second sealing means 42, 46.

As shown in FIGS. 1 to 8, the fluid chamber 18 is sidely or circumferentially confined by a tubular wall 54 of the housing 12 and longitudinally confined by the first sealing means 42 and the second sealing means 46. Further, the first compartment 24 is fluidly isolated from the second compartment 26 by means of the first sealing means 42 and the first internal separating wall 28, wherein the third compartment 34 is fluidly isolated from the fourth compartment 36 by means of the second sealing means 46 and the first internal separating wall 38.

The filter device shown in FIGS. 1 to 7 further comprises a sixth fluid port 23 arranged at the second compartment 26 of the first lid 20, the sixth fluid port 23 being closed by a closing means 56 such as a cap. This is advantageous for a symmetric form of the filter device 10 with respect to a middle surface at half-length of the housing 12.

The first group of hollow fibers 40a may comprise more fibers than the second group of hollow fibers 40b. For instance, the first group of hollow fibers 40a may comprise at least 70% of the entire amount of hollow fibers 40 arranged within the housing 12 of the filter device 10.

The filter device 10 according to the present invention may be configured as a dialyser and is applicable for different types of dialysis, for instance in haemodialysis (HD), haemofiltration (HF), haemodiafiltration (HDF).

FIG. 2A shows schematically a system 58a for filtration of fluids according to an embodiment of the present invention. The system 58a comprises a filter device 10 as shown in FIG. 1 and a substitution fluid line 60 for fluidly connecting the third fluid port 33 of the filter device 10 selectively either to the first fluid port 22/arterial line 62 or to the second fluid port 32/venous line 64 depending on if a pre- or post-dilution treatment is desired. The substitution fluid line 60 is arranged outside the housing 12 of the filter device 10.

Figure 2:
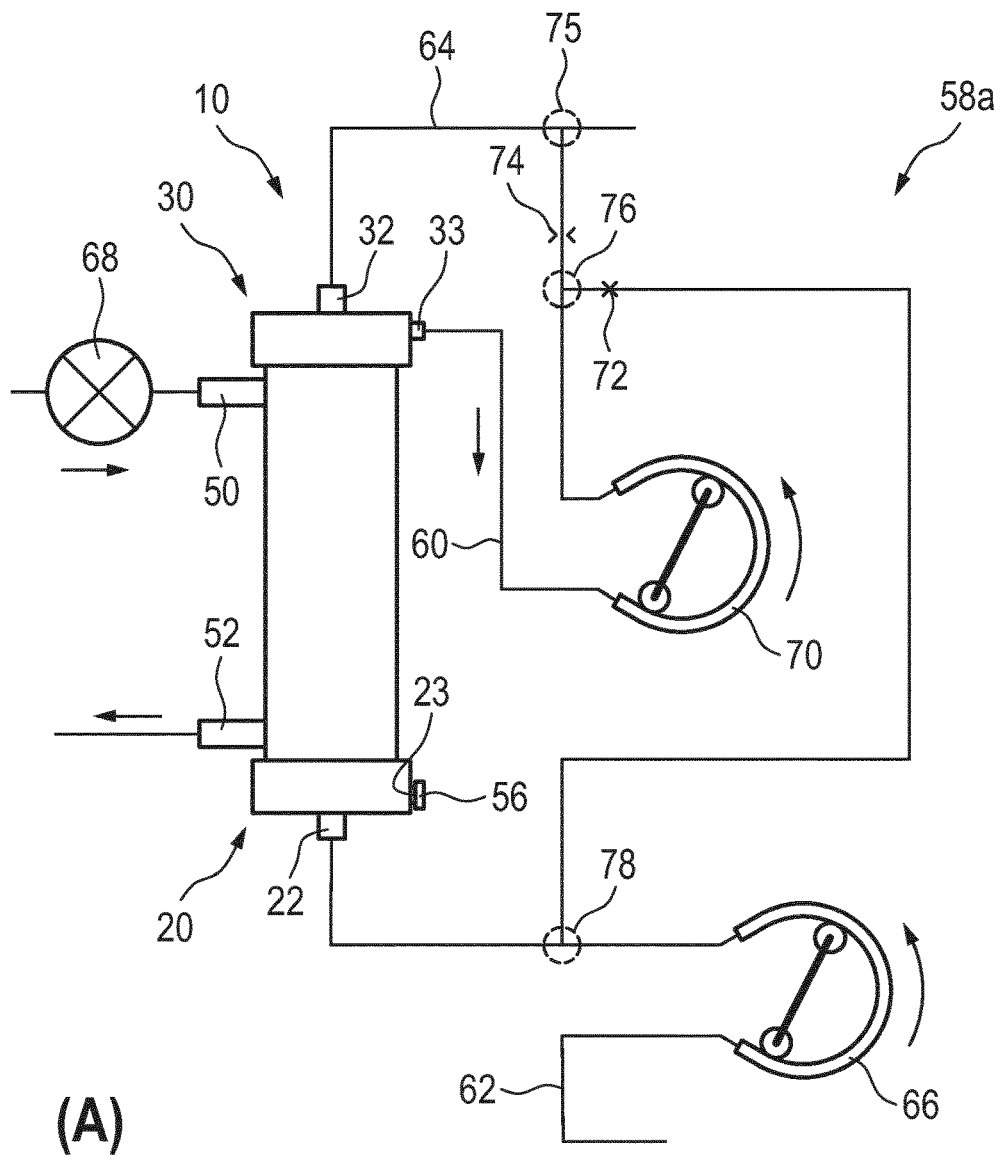
FIG. 2A schematically shows a system according to an embodiment, the system comprising the filter device shown in FIG. 1.
FIG. 2B shows a method for filtration of fluids according to an embodiment using the filter device shown in FIG. 1, in particular using the system shown in FIG. 2A.
Figure 2:
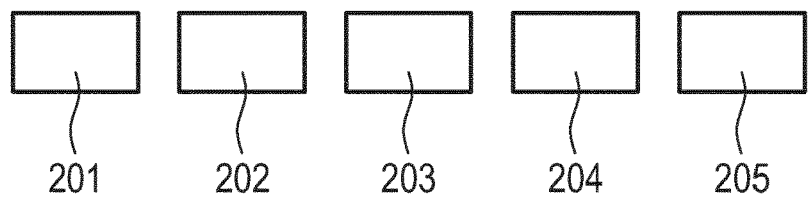

The system 58a in FIG. 2 further comprises an arterial line 62 for fluidly connecting an arterial side of a patient access to the first fluid port 22 of the filter device 10 and a venous line 64 for fluidly connecting a venous side of the patient access to the second fluid port 32 of the filter device 10. In addition, the system 58a comprises a first pump being an arterial pump 66 for pumping a first fluid into the first fluid port 22. Alternatively or additionally, a venous pump may be provided for draining the first fluid from the second fluid port 32 of the filter device 10. A second pump 68 is provided for pumping a second fluid into the fourth fluid port 50. Alternatively or additionally, a pump may be provided for draining the second fluid from the fifth fluid port 52 of the filter device 10.

As shown in the embodiment of FIG. 2, the substitution fluid line 60 is fluidly connected to the arterial line 62 at a port 78 and to the venous line 64 at another port 75.

FIG. 2B shows a method for filtration of fluids according to the present invention using the filter device 10 shown in FIG. 1 or 6. In step 201, blood from the arterial side of a patient access is introduced into the filter device 10 through the arterial line 62 and subsequently through the first fluid port 22, wherein this step is preferably facilitated by the arterial pump 66. In step 202, the introduced artery blood is directed from the first lid 20 to the second lid 30 of the filter device 10 via the first compartment 24, the first group of hollow fibers 40a and the second compartment 26 in this order. In step 203, the directed blood is drained from the filter device 10 through the second fluid port 32, wherein this step may be facilitated by a venous pump (not shown).

In step 204, a dialysis fluid is introduced into the filter device 10 through the fourth fluid port 50, wherein this step is preferably facilitated using the inlet dialysis pump 68. In step 205, the introduced dialysis fluid is drained from the filter device 10 through the fifth fluid port 52, wherein this step may be facilitated using an outlet dialysis pump (not shown). After the dialysis fluid has been introduced into the fluid chamber 18 of the filter device 10, a fluid connection between the fourth fluid port 50 and the first and second group of hollow fibers 40a, 40b enables the dialysis fluid to reach the fibers 40a, 40b via the fluid chamber 18.

In another step, a third fluid, in particular useful fluids such as substitution fluids, infusion fluids and/or buffer fluids may be produced by filtering the second fluid (dialysis fluid). The second fluid is preferably filtered into the second group of hollow fibers 40b through the semi-permeable membranes of the fibers 40b. The second fluid may permeate into the internal fluid channels of the second group of hollow fibers 40b through the semi-permeable membranes of these fibers 40b such that the second fluid is thereby filtered. This filtered second fluid is (or may be used as) the third fluid (substitution fluid). Subsequently, the third fluid is preferably drained from the filter device 10 by flowing from the internal channels of the second group of fibers 40b to the third fluid port 33 via the fourth compartment 36 (FIGS. 1 and 6), before entering the substitution fluid line 60. This is preferably facilitated by the pump 70.

According to the embodiment of FIG. 2, the substitution fluid line 60 may be connected selectively either to the arterial line 62 or to the venous line 64. A predilution mode can be achieved by operating a valve 74 between the venous line 64 and the substitution fluid line 60 in a closed state and by operating a valve 72 between the arterial line 62 and the substitution fluid line 60 in an opened state. In this configuration, the third fluid produced as described above can be pumped from the third fluid port 33 to the port 78 via the opened valve 72. At the port 78, the third fluid is mixed to the blood from the arterial side of the patient access before being introduced to the filter device 10 again.

Further, a post-dilution mode can be achieved by operating the valves 72 and 74 in a reverse manner with respect to the pre-dilution state, i.e. the valve 72 in a closed state and the valve 74 in an opened state. In this configuration, the third fluid produced as described above can be pumped from the third fluid port 33 to the port 75 via the opened valve 74. At the port 75, the third fluid is mixed to the filtered blood from the second fluid port 32 of the filter device 10 before entering the venous side of the patient access.

Figure 3:
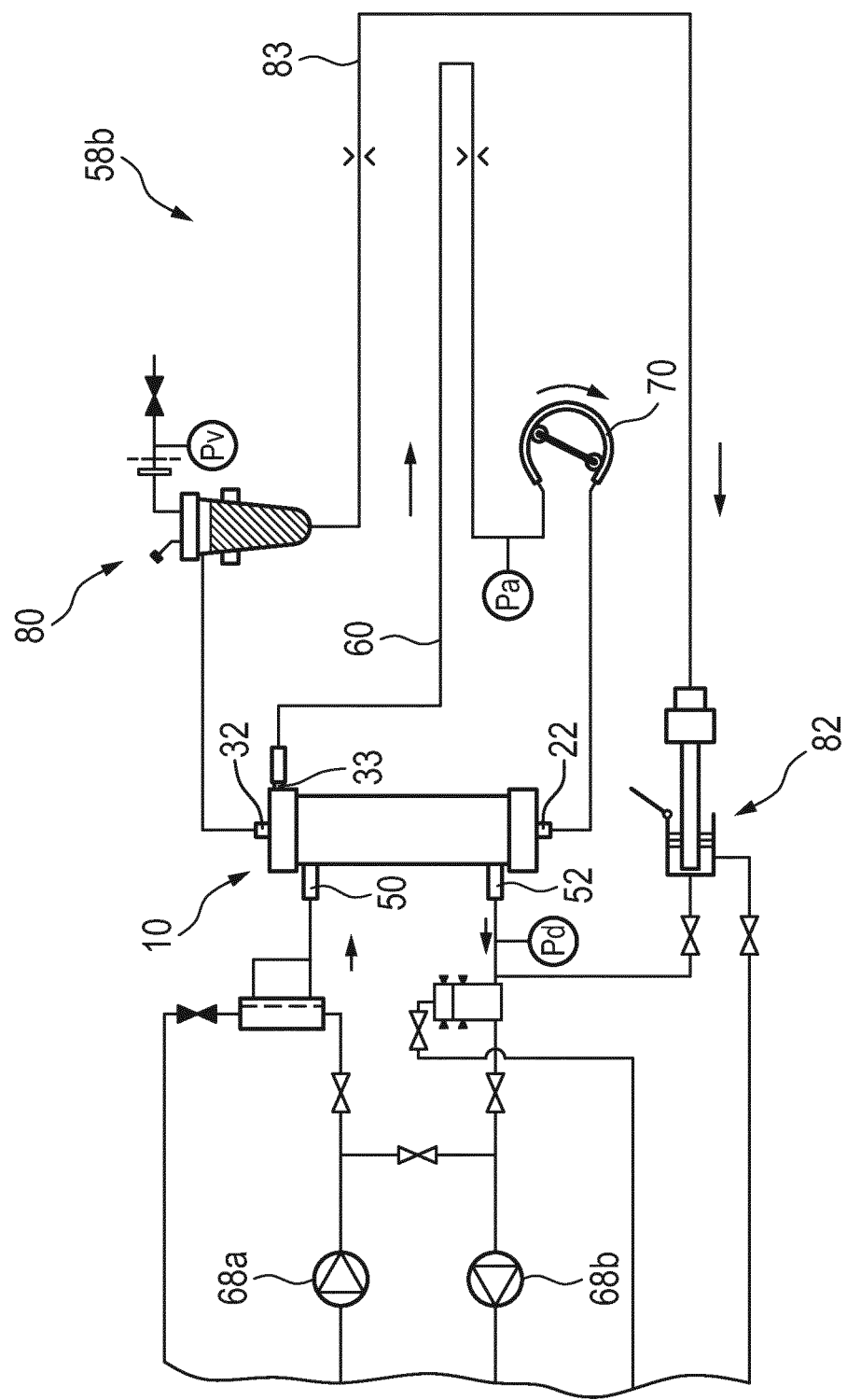
FIG. 3 shows a system according to another embodiment.

FIG. 3 shows schematically a system 58b according to another embodiment of the present invention. The system 58b comprises a filter device 10 as shown in FIGS. 1-2 and a substitution fluid line 60 as shown in FIG. 2. Further, the system 58b comprises a line 83 for fluidly connecting the second fluid port 32 of the filter device 10 to a waste handling unit 82. The waste handling unit 82 is preferably a waste handling option (WHO) for further processing the waste. Preferably, the line 83 comprises a venous drip chamber 80 for detecting and/or collecting air bubbles, thereby increasing the safety of the system 58b. The venous drip chamber 80 is important during dialysis treatment, but has no function during priming. As shown in FIG. 3, two dialysis pumps 68a, 68b are connected each to one of the fourth and fifth fluid port 50, 52, respectively, wherein the arrows shown at the pumps 68a, 68b indicate the pumping directions.

FIG. 4 shows schematically a system 58c according to another embodiment of the present invention. The system 58c is similar to the system 58b shown in FIG. 3, except that the line 83 here is connected not to a waste handling unit, but a waste bag 84.

All systems 58a, 58b, 58c shown in FIGS. 2-4 are preferably configured to contain only one or two additional filters in the dialysis fluid path in addition to the filter device 10. This enables to use only two or three filters in total in the system, including the filter device 10 itself, to perform filtration, in particular to produce substitution fluids by filtering the substitution fluids through these filters. Advantageously, the filter device is/are single use filter(s).

Hollow fiber membranes which can be used in the device 10 according to all aspects of the systems and methods according to the invention can be so-called high-flux membranes. Also, now-flux membranes in combination with ultra high-flux membranes may be used. High-flux membranes are conventional dialysis membranes. They are classified as "high-flux" membranes in distinction to "low-flux" membranes depending on their permeability. High-flux membranes used in devices, such as, for example, the Polyflux® H-series of Gambro, the Revaclear® dialyzers of Gambro and the Ultraflux® EMIC2 or Optiflux® F180NR dialyzer of Fresenius Medical Care have been on the market for several years now. The high-flux membranes used therein are mainly polysulfone or polyethersulfone based membranes and methods for their production have been described, for example, in U.S. Pat. No. 5,891,338 or EP 2 113 298 A1. Another polyphenylene membrane which is known as a high-flux membrane is used in the Phylther® HF 17G filter from Bellco Società unipersonale a r.l. The expression "high-flux membrane(s)" as used herein generally refers to membranes having a MWRO between 5 kDa and 10 kDa and a MWCO between 25 kDa and 65 kDa, as determined by dextran sieving measurements according to Boschetti et al. (Extended characterization of a new class of membranes for blood purification: The high cut-off membranes. Int J Artif Organs 2013; 36(7), 455-463)). Their average pore radius is in the range of from 3.5 to 5.5 nm, wherein the pore size is determined from the MWCO based on dextran sieving coefficients according to Boschetti-de-Fierro et al. (2013). The packing density of the hollow fiber membranes in the devices of the present invention is from 35% to 68%, i.e., the sum of the cross-sectional area of all hollow fiber membranes present in the dialyzer amounts to 35 to 68% of the cross-sectional area of the part of the housing comprising the bundle of semi-permeable hollow fiber membranes. According to one embodiment of the present invention, the packing density of the hollow fiber membranes in the devices of the present invention is from 45% to 60%. If n hollow fiber membranes are present in the bundle of semi-permeable hollow fiber membranes, $D_F$ is the outer diameter of a single hollow fiber membrane, and $D_H$ is the inner diameter of the part of the dialyzer housing comprising the bundle, the packing density can thus be calculated according to $n*(D_F/D_H)^2$.

The filter device 10 and systems shown in FIGS. 1 to 8 may be used to perform priming and/or rinse-back of the filter device 10.

The filter device 10, in particular a dialyser, may normally be delivered in a dry state. In the preparation of dialysis-type treatments, the dialyser is first filled and flown through with an aqueous physiological solution or priming fluid. This process is referred to as dialyser preparation or priming. Such a priming fluid is normally extracted from an external saline bag containing a saline fluid.

Using the filter device 10 or the systems according to the present invention, the priming can be done by producing a priming fluid based on the dialysis fluid, using the way to produce the third fluid described above. In particular, the priming fluid can be generated by filtering the third fluid out of the introduced dialysis fluid and by directing the third fluid to enter the first fluid port 22 via the substitution fluid line 60. The pump 70 may facilitates this process. The dialysis fluid is normally not suitable to be used directly as priming fluid due to the contaminants contained in it. The present invention therefore enables to produce a priming fluid and to perform priming of the filter device 10 and/or the hollow fibers 40 without using any saline bag.

The process of rinse-back is performed after filtration of fluids, in particular after the dialysis-type treatment has almost been completed. The remainder of filtered fluid, e.g. blood, needs to be pumped into the venous line to enter the venous side of the patient access. This is normally done using a saline fluid from a saline bag as rinse-back fluid.

Using the filter device 10 or the systems according to the present invention, the rinse-back can be done by producing a rinse-back fluid based on the dialysis fluid, using the way to produce the third fluid described above. In particular, the rinse-back fluid can be generated by filtering the third fluid out of the introduced dialysis fluid and by directing the third fluid to enter the first fluid port 22 via the substitution fluid line 60. This process may be facilitated by the pump 70. The dialysis fluid is normally not suitable to be used directly as rinse-back fluid due to the contaminants contained in it. The present invention therefore enables to produce a rinse-back fluid and to perform priming of the filter device 10 and/or the hollow fibers 40 without using any saline bag.

A still further embodiment of a system 58d including the device 10 according to the present invention is schematically shown in FIG. 5. This embodiment shall, inter alia, illustrate that the device 10 according to the present invention is not restricted to the flow directions described above with reference to the systems 58a, 58b, 58c according to the embodiments shown in FIGS. 2-4. Hence could any of the fluid ports 50 and 52 be an inlet while the other is an outlet. The same is true for the fluid ports 22 and 32. Moreover, the first fluid is not restricted to flow inside the first group of fibers 40a. It could equally well flow outside the fibers 40a, 40b while the second fluid is instead flowing inside the fibers 40a. In such a setting the substitution fluid is created by instead introducing dialysis fluid into port 33 or 23 and let it be filtered when passing from the interior to the exterior of the second group of fibers 40b. In a dialysis treatment situation this means that the substitution fluid is mixed with the blood inside the dialyzer 10.

In the embodiment schematically illustrated in FIG. 5, blood from the arterial side of the patient access is pumped by pump 66' from the arterial line 62 into the fifth fluid port 52. The fourth fluid port 50 is connected to the venous line 64. The blood thus flows through the fluid chamber 18 of the device 10 outside the fibers 40a, 40b. A part of the dialysis fluid in this embodiment enters the device 10 at the second fluid port 32, flows inside the first group of fibers 40a, and leaves the device 10 again at the first fluid port 22. The other part of the dialysis fluid enters the device 10 at the third fluid port 33 and flows via the fourth compartment 36 into the interior of the second group of hollow fibers 40b. Substitution fluid is created by let this part of the dialysis fluid be filtered when passing from the interior to the exterior of the second group of fibers 40b. The substitution fluid may then be mixed with the blood in the fluid chamber 18 outside of the fibers 40a, 40b, and may then leave the device 10 together with the blood at the fourth fluid port 50.

If the device 10 is operated in the way shown in FIG. 5, a special type of hollow fiber membranes is preferably used. Hollow fiber membranes which can be used in the embodiment shown in FIG. 5 are membranes wherein the blood is in contact with the outside of the membrane and the dialysis fluid is channeled through the lumen of the hollow fibers. Such membranes are known in the art and have been described, for example, in WO 2008/046779 A1. Further considerations as concerns the use of membranes having their selective layer on the outside have been provided for in US 2015/0314057 A1. Packing densities in this case are calculated as described before and will advantageously lie in the range of from 30% to 60%.

FIG. 6 shows a system according to a first aspect of the system according to the invention, whereby the features as explained and described for the embodiment as shown in FIGS. 1 to 5, that are shared by the systems according to the inventions are referred to with the same reference numbers. It is to be understood that the features shared by the embodiment shown in FIGS. 1 to 5 and shown in FIGS. 6 to 8 have the same function in the systems as shown in FIGS. 6 to 8 as described for the system/filter device as shown in FIGS. 1 to 5, and in this regard the same disclosure shall apply.

The system as shown in FIG. 6 comprises a filter device 10, which comprises a housing 12 having a first end 14 and a second end 16 and defining a fluid chamber 18 extending between the first end 14 and the second end 16; further a first lid 20 provided at the first end 14 of the housing 12 and comprising a first fluid port 22, a first compartment 24, a second compartment 26 and a first internal separating wall 28 separating the first compartment 24 from the second compartment 26. The filter device 10 further comprises a second lid 30 provided at the second end 16 of the housing 12 and comprising a second fluid port 32, a third fluid port 33, a third compartment 34, a fourth compartment 36 and a second internal separating wall 38 separating the third compartment 34 from the fourth compartment 36.

Within the housing 12, a plurality of hollow fibers 40 is arranged, wherein each of the plurality of hollow fibers 40 comprises a semi-permeable membrane and defines a fluid channel extending longitudinally through an interior of the respective hollow fiber 40. The semi-permeable membrane is preferably configured to allow substances, whose size is below a threshold size, to enter the internal fluid channel from exterior of the fiber and/or to exit the internal fluid channel to the exterior of the fiber. Also, a first sealing means 42 which separates the fluid chamber 18 from the first and the second compartment 24, 26 is provided, the first sealing means 42 having a first longitudinal end 44 facing away from the second lid 30, as well as a second sealing means 46 which separates the fluid chamber 18 from the third and the fourth compartment 34, 36, the second sealing means 46 having a second longitudinal end 48 facing away from the first lid 20.

Further, the filter device 10 comprises a fourth fluid port 50 and a fifth fluid port 52 both provided at the fluid chamber 18 and located between the first longitudinal end 44 of the first sealing means 42 and the second longitudinal end 48 of the second sealing means 46, wherein the first fluid port 22 is arranged at the first compartment 24, the second fluid port 32 is arranged at the third compartment 34, and wherein the third fluid port 33 is arranged at the fourth compartment 36.

The plurality of hollow fibers 40 comprises a first group of fibers 40a and a second group of fibers 40b, wherein (substantially) each hollow fiber of the first group of fibers 40a extends from the first compartment 24 through the fluid chamber 18 to the third compartment 34 and, for directing a first fluid, fluidly connects the first compartment 24 with the third compartment 34 via the fluid channels extending through the interior of each hollow fiber of the first group of fibers 40a, and wherein each hollow fiber of the second group of fibers 40b extends from the second compartment 26 through the fluid chamber 18 to the fourth compartment 36 and, for directing a second fluid, fluidly connects the second compartment 26 with the fourth compartment 36 via the fluid channels extending through the interior of each hollow fiber of the second group of fibers 40b.

The fourth and the fifth fluid port 50, 52 are fluidly connected to one another and both in fluidic communication with an exterior of both the hollow fibers of the first and the second group of fibers 40a, 40b via the fluid chamber 18.

Also, the system further comprises a line 64a for draining the first fluid from the third compartment 34 and from the second fluid port 32 of the filter device 10. As can be seen in FIG. 6, there is also provided a substitution fluid line 60a for draining the second fluid from the fourth compartment 36, the substitution fluid line 60a, at a connection site 75, being fluidly connected to the line 64a for diluting or mixing the first with the second fluid. The line 64a and the substitution line 60a are being arranged outside the housing 12 of the filter device 10. The line 64a, in addition, comprises a flow reducing means 88, the flow reducing means 88 being positioned between the second fluid port 32 and the connection site 75.

Accordingly, with the system shown in FIG. 6, the following method for filtration and/or dilution of a first fluid with a second fluid can be performed: A first fluid is introduced into the filter device 10 through the first fluid port 22; subsequently, the first fluid is directed from the first lid 20 to the second lid 30 via the first compartment 24, the fluid channels in the interior of the first group of hollow fibers 40a and to the third compartment 34. Then the first fluid is drained from the filter device 10 through the second fluid port 32 via line 64, and, subsequently or parallel, a second fluid is introduced into the filter device 10 through the fourth fluid port 50. Subsequently, a first part of the second fluid is drained from the filter device 10 through the fifth fluid port 52, while a second part of the second fluid is filtered by guiding it from the fourth fluid port 50 via the fluid chamber 18 to the exterior of the second group of hollow fibers 40b, through the semi-permeable membranes of the second group of hollow fibers 40b into the fluid channels in the interior of the second group of hollow fibers 40b and to the third fluid port 33. Next, the filtered second part of the second fluid is drained from the filter device 10 through the third fluid port 33 via substitution fluid line 60a, thereby diluting the filtered first fluid with the filtered second part of the second fluid either directly via the connection site or by actively and fluidly connecting the substitution fluid line 60a with the line 64a.

In the system in FIG. 6, the flow reducing means 88 reduce the flow of the first fluid through the line 64a, thereby creating a relative pressure difference between the fourth fluid port 50 and the third fluid port 33 (the substitution fluid line 60a), causing the second fluid, which is present in the fluid chamber 18, to enter the semi-permeable membranes and the fluid channels extending though the interior of the hollow fibers of the second group of fibers 40b, and subsequently, to enter the fourth compartment 36 in the second lid 30. Via the fourth compartment 36, and still necessitated by the pressure difference caused by the flow reducing means 88, the second fluid, or rather a part of the second fluid, is drained from the third fluid port 33 into the substitution fluid line 60a, thus diluting the first fluid guided within the line 64a.

Alternatively or additionally, a venous pump may be provided connected to the line 64a after the connecting site 75 of the line 64a and the substitution fluid line 60a.

Also, according to an alternative embodiment of the system of FIG. 6 (which alternative system is not shown as a whole in the figures), instead of the first lid 20 comprising two compartments 24, 26, the lid 20 can be provided with a single compartment 24a as shown (and described below) for the system displayed in FIG. 8. In this case it is mandatory that the second group of fibers is provided with closed ends in the first compartment (as it is schematically indicated in FIG. 8 by the letter a), so that there is no fluid connection between the first compartment 24a with the fourth compartment 36. Nevertheless, since the hollow fibers are only closed at their respective first end 90, the fluid channels extend from the closed first end 90 through the interior of each hollow fiber of the second group of fibers to the fourth compartment 36.

FIG. 7 shows a system according to a second aspect of the present invention: The filter device (10) of the system shown in FIG. 7 also comprises a housing 12 having a first end 14 and a second end 16 and defining a fluid chamber 18 extending between the first end 14 and the second end 16, as well as a first lid 20 provided at the first end 14 of the housing 12 and comprising a first fluid port 22, a first compartment 24, a second compartment 26 and a first internal separating wall 28 separating the first compartment 24 from the second compartment 26.

The filter device 10 of the system as shown in FIG. 7 also comprises a second lid 30 provided at the second end 16 of the housing 12 and comprising a second fluid port 32 and a second lid compartment 34b, the second lid compartment 34b representing a single compartment not being separated by internal separating means.

As the filter devices shown in FIG. 6, also the filter device 10 shown in FIG. 7 further comprises a plurality of hollow fibers 40 arranged within the housing 12, wherein each of the plurality of hollow fibers 40 comprises a semi-permeable membrane and defines a fluid channel extending longitudinally through an interior of the respective hollow fiber 40. Further, a first sealing means 42 is provided, which separates the fluid chamber 18 from the first and the second compartment 24, 26. The first sealing means 42 also has a first longitudinal end 44 facing away from the second lid 30. In addition, a second sealing means 46 is provided, which separates the fluid chamber 18 from the second lid compartment 34b, wherein the second sealing means 46 has a second longitudinal end 48 facing away from the first lid 20.

The filter device also comprises a fourth fluid port 50 and a fifth fluid port 52, which are both provided at the fluid chamber 18 and are located between the first longitudinal end 44 of the first sealing means 42 and the second longitudinal end 48 of the second sealing means 46. The first fluid port 22 is arranged at the first compartment 24, wherein the second fluid port 32 is arranged at the second lid compartment 34b.

As can be seen in FIG. 7, the plurality of hollow fibers 40 comprises a first group of fibers 40a and a second group of fibers 40b, wherein each hollow fiber of the first group of fibers 40a extends from the first compartment 24 through the fluid chamber 18 to the second lid compartment 34b and fluidly connects the first compartment 24 with the second lid compartment 34b via the fluid channels extending through the interior of each hollow fiber of the first group of fibers 40a for filtering a first fluid.

Also, each hollow fiber of the second group of fibers 40b extends from the second compartment 26 through the fluid chamber 18 to the second lid compartment 34b and fluidly connects the second compartment 26 with the second lid compartment 34b via the fluid channels extending through the interior of each hollow fiber of the second group of fibers 40b.

In the system as shown in FIG. 7, the fourth and the fifth fluid port 50, 52 are fluidly connected to one another and both in fluidic communication with an exterior of both the hollow fibers of the first and the second group of fibers 40a, 40b via the fluid chamber 18.

FIG. 8 shows a system according to a third aspect of the invention, and also comprises a filter device 10. The filter device 10 of the system shown in FIG. 8 comprises a housing 12 having a first end 14 and a second end 16 and defining a fluid chamber 18 extending between the first end 14 and the second end 16. The filter device further comprises a first lid 20 provided at the first end 14 of the housing 12 and comprising a first fluid port 22 and a first compartment 24a, which represents a single compartment that is not being separated by internal separating means. Also provided is a second lid 30 provided at the second end 16 of the housing 12 and comprising a second fluid port 32 and a second lid compartment 34c, wherein the second lid compartment 34c represents a single compartment that is not being separated by internal separating means.

The filter device 10 of the system shown in FIG. 8 also comprises a plurality of hollow fibers 40 arranged within the housing 12, wherein each of the plurality of hollow fibers 40 comprises a semi-permeable membrane and defines a fluid channel extending longitudinally through an interior of the respective hollow fiber 40.

Further, a first sealing means 42 is provided, which separates the fluid chamber 18 from the first compartment 24a, wherein the first sealing means 42 has a first longitudinal end 44 facing away from the second lid 30, as well a second sealing means 46 which separates the fluid chamber 18 from the second lid compartment 34c, wherein the second sealing means 46 has a second longitudinal end 48 facing away from the first lid 20.

The system further comprises a third fluid port 50 and a fourth fluid port 52 both provided at the fluid chamber 18 and located between the first longitudinal end 44 of the first sealing means 42 and the second longitudinal end 48 of the second sealing means 46.

In the system shown in FIG. 8, the first fluid port 22 is arranged at the first compartment 24a, and the second fluid port 32 is arranged at the second lid compartment 34c. Also, the plurality of hollow fibers 40 comprises a first group of fibers 40a and a second group of fibers 40c, with each hollow fiber of the first 40a and the second 40c group of fibers comprising a first end 90 and a second end 92, wherein each hollow fiber of the first group of fibers 40a extends via its respective first end 90 from the first compartment 24a through the fluid chamber 18 to, via its second end 92, the second lid compartment 34c, and, for directing a first fluid, fluidly connects the first compartment 24a with the second lid compartment 34c via the fluid channels extending through the interior of each hollow fiber of the first group of fibers 40a.

Further, in the system shown in FIG. 8, each hollow fiber of the second group of fibers 40c substantially extends, via its respective first end 90, from the first compartment 24a through the fluid chamber 18 to, via its respective second end 92, the second lid compartment 34c, wherein each hollow fiber of the second group of fibers 40c at its respective first end 90 is closed as it is schematically indicated in FIG. 8 by the letter a, so that there is no fluid connection between the first compartment 24a with the second lid compartment 34c. Nevertheless, since the hollow fibers are only closed at their respective first end 90, the fluid channels extend from the closed first end 90 through the interior of each hollow fiber of the second group of fibers 40c to the second lid compartment 34c.

Further, in the system shown in FIG. 8, the fourth and the fifth fluid port 50, 52 are fluidly connected to one another and both in fluidic communication with an exterior of both the hollow fibers of the first and the second group of fibers 40a, 40b via the fluid chamber 18.

With the systems according to the second and third aspect and as exemplarily shown in FIGS. 7 and 8, an exemplary method for filtration and/or dilution of a first fluid with a second fluid can be performed, that is described as follows. Firstly, a first fluid is introduced into the filter device 10 through the first fluid port 22, where it is subsequently directed from the first lid 20 to the second lid 30, namely via the first compartment 24; 24a and the fluid channels in the interior of the first group of hollow fibers 40a into the second lid compartment 34b; 34c.

Subsequently or simultaneously, a second fluid is introduced into the filter device 10 through the fourth fluid port 50. Next, a first part of the second fluid is drained from the filter device 10 through the fifth fluid port 52, and a second part of the second fluid is filtered by guiding it from the fourth fluid port 50 via the fluid chamber 18 to the exterior of the second group of hollow fibers 40b, through the semi-permeable membranes of the second group of hollow fibers 40b into the fluid channels in the interior of the second group of hollow fibers 40b and into the second lid compartment 34b, 34c, thereby diluting the first fluid with the second fluid.

Optionally, the diluted mixture of the first and the second fluid can be drained from the filter device 10 through the second fluid port 32.

The invention claimed is:

1. A system comprising a filter device for filtration of fluids, wherein said filter device comprises:
a housing having a first end and a second end and defining a fluid chamber extending between the first end and the second end;
a first lid provided at the first end of the housing and comprising a first fluid port, a first compartment, a second compartment and a first internal separating wall separating the first compartment from the second compartment;
a second lid provided at the second end of the housing and comprising a second fluid port, a third fluid port, a third compartment, a fourth compartment and a second internal separating wall separating the third compartment from the fourth compartment;
a plurality of hollow fibers arranged within the housing, wherein each of the plurality of hollow fibers comprises a semi-permeable membrane and defines a fluid channel extending longitudinally through an interior of the respective hollow fiber;
a first sealing means which separates the fluid chamber from the first compartment and the second compartment, the first sealing means having a first longitudinal end facing away from the second lid;
a second sealing means which separates the fluid chamber from the third and the fourth compartment, the second sealing means having a second longitudinal end facing away from the first lid;
a fourth fluid port and a fifth fluid port both provided at the fluid chamber and located between the first longitudinal end of the first sealing means and the second longitudinal end of the second sealing means;
wherein the first fluid port is arranged at the first compartment, wherein the second fluid port is arranged at the third compartment, wherein the third fluid port is arranged at the fourth compartment,
wherein the plurality of hollow fibers comprises a first group of fibers and a second group of fibers, wherein each hollow fiber of the first group of fibers extends from the first compartment through the fluid chamber to the third compartment and, for directing a first fluid, fluidly connects the first compartment with the third compartment via the fluid channels extending through the interior of each hollow fiber of the first group of fibers, and wherein each hollow fiber of the second group of fibers extends from the second compartment through the fluid chamber to the fourth compartment and, for directing a second fluid, fluidly connects the second compartment with the fourth compartment via the fluid channels extending through the interior of each hollow fiber of the second group of fibers, wherein the fluid chamber does not have provided therein a wall to separate the first group of hollow fibers and the second group of hollow fibers, and,
wherein the fourth fluid port and the fifth fluid port are fluidly connected to one another and both in fluidic communication with an exterior of both the hollow fibers of the first group of fibers and the second group of fibers via the fluid chamber,
wherein the system further comprises a line for draining the first fluid from the third compartment and from the second fluid port of the filter device;
and wherein the system further comprises a substitution fluid line for draining the second fluid from the fourth compartment, the substitution fluid line, at a connection site, being fluidly connected to the line for diluting or mixing the first with the second fluid, wherein the line and the substitution line are being arranged outside the housing of the filter device,
and wherein the line comprises a flow reducing means, the flow reducing means being positioned between the second fluid port and the connection site.

2. The system according to claim 1, wherein the flow reducing means is controllable.

3. A system comprising a filter device for filtration of fluids, wherein said filter device comprises:

a housing having a first end and a second end and defining a fluid chamber extending between the first end and the second end;

a first lid provided at the first end of the housing and comprising a first fluid port, a first compartment, a second compartment and a first internal separating wall separating the first compartment from the second compartment;

a second lid provided at the second end of the housing and comprising a second fluid port and a second lid compartment, the second lid compartment representing a single compartment not being separated by internal separating means;

a plurality of hollow fibers arranged within the housing, wherein each of the plurality of hollow fibers comprises a semi-permeable membrane and defines a fluid channel extending longitudinally through an interior of the respective hollow fiber;

a first sealing means which separates the fluid chamber from the first compartment and the second compartment, the first sealing means having a first longitudinal end facing away from the second lid;

a second sealing means which separates the fluid chamber from the second lid compartment, the second sealing means having a second longitudinal end facing away from the first lid;

a fourth fluid port and a fifth fluid port both provided at the fluid chamber and located between the first longitudinal end of the first sealing means and the second longitudinal end of the second sealing means;

wherein the first fluid port is arranged at the first compartment, wherein the second fluid port is arranged at the second lid compartment, wherein the plurality of hollow fibers comprises a first group of fibers and a second group of fibers, wherein each hollow fiber of the first group of fibers extends from the first compartment through the fluid chamber to the second lid compartment and fluidly connects the first compartment with the second lid compartment via the fluid channels extending through the interior of each hollow fiber of the first group of fibers for filtering a first fluid, and wherein each hollow fiber of the second group of fibers extends from the second compartment through the fluid chamber to the second lid compartment and fluidly connects the second compartment with the second lid compartment via the fluid channels extending through the interior of each hollow fiber of the second group of fibers, and wherein the fluid chamber does not have provided therein a wall to separate the first group of hollow fibers and the second group of hollow fibers, and wherein the fourth fluid port and the fifth fluid port are fluidly connected to one another and both in fluidic communication with an exterior of both the hollow fibers of the first group of fibers and the second group of fibers via the fluid chamber.

4. A system comprising a filter device for filtration of fluids, wherein said filter device comprises:

a housing having a first end and a second end and defining a fluid chamber extending between the first end and the second end;

a first lid provided at the first end of the housing and comprising a first fluid port and a first compartment, the first compartment being a single compartment and not being separated by internal separating means;

a second lid provided at the second end of the housing and comprising a second fluid port and a second lid compartment, the second lid compartment being a single compartment and not being separated by internal separating means;

a plurality of hollow fibers arranged within the housing, wherein each of the plurality of hollow fibers comprises a semi-permeable membrane and defines a fluid channel extending longitudinally through an interior of the respective hollow fiber;

a first sealing means which separates the fluid chamber from the first compartment, the first sealing means having a first longitudinal end facing away from the second lid;

a second sealing means which separates the fluid chamber from the second lid compartment, the second sealing means having a second longitudinal end facing away from the first lid;

a third fluid port and a fourth fluid port both provided at the fluid chamber and located between the first longitudinal end of the first sealing means and the second longitudinal end of the second sealing means;

wherein the first fluid port is arranged at the first compartment, wherein the second fluid port is arranged at the second lid compartment, wherein the plurality of hollow fibers comprises a first group of fibers and a second group of fibers, with each hollow fiber of the first and the second group of fibers comprising a first end and a second end, wherein each hollow fiber of the first group of fibers extends via its respective first end from the first compartment through the fluid chamber to, via its second end, the second lid compartment, and, for directing a first fluid, fluidly connects the first compartment with the second lid compartment via the fluid channels extending through the interior of each hollow fiber of the first group of fibers, and wherein each hollow fiber of the second group of fibers substantially extends, via its respective first end, from the first compartment through the fluid chamber to, via its respective second end, the second lid compartment, wherein each hollow fiber of the second group of fibers at its respective first end is closed, so that there is no fluid connection between the first compartment with the second lid compartment through the second group of fibers, with the fluid channels extending from the closed first end through the interior of each hollow fiber of the second group of fibers to the second lid compartment, and wherein the fourth fluid port and the fifth fluid port are fluidly connected to one another and both in fluidic communication with an exterior of both the hollow fibers of the first group of fibers and the second group of fibers via the fluid chamber.

5. The system according to claim 1, wherein the fourth fluid port and the fifth fluid port are in direct fluid connection to the fluid chamber, the direct fluid connection being located between the first longitudinal end of the first sealing means and the second longitudinal end of the second sealing means.

6. The system according to claim 1, wherein the fluid chamber is spatially confined by an inner wall of the housing, the first sealing means and the second sealing means.

7. The system according to claim 1, wherein the first compartment is fluidly isolated from the second compartment by means of the first sealing means and the first internal separating wall.

8. The system according to claim 1, wherein the first sealing means and/or the second sealing means comprises a potting compound for receiving the first group of fibers and/or the second group of hollow fibers.

9. The system according to claim 1 further comprising a sixth fluid port arranged at the second compartment of the first lid, the sixth fluid port being closed by a closing means.

10. The system according to claim 1, wherein the first group of hollow fibers comprise more fibers than the second group of hollow fibers (40b).

11. The system according to claim 1, further comprising:
an arterial line for fluidly connecting an arterial side of a patient access to the first fluid port of the filter device;
a venous line for fluidly connecting a venous side of the patient access to the second fluid port of the filter device;
a first pump for pumping a first fluid into the first fluid port and/or for draining the first fluid from the second fluid port of the filter device; and
a second pump for pumping a second fluid into the fourth fluid port and/or for draining the second fluid from the fifth fluid port of the filter device.

12. The system according to claim 11, wherein the substitution fluid line is fluidly connected to the venous line.

13. The system according to claim 1, further comprising a line for fluidly connecting the second fluid port of the filter device to a waste handling unit and/or a waste bag.

14. The system according to claim 1, further containing one or two additional filters in addition to the filter device.

15. The system according to claim 1, wherein the flow reducing means is non-controllable.

16. The system according to claim 10, wherein the first group of hollow fibers comprise at least 70% of the plurality of hollow fibers.

17. The system according to claim 3, wherein the fourth fluid port and the fifth fluid port are in direct fluid connection to the fluid chamber, the direct fluid connection being located between the first longitudinal end of the first sealing means and the second longitudinal end of the second sealing means.

18. The system according to claim 4, wherein the fourth fluid port and the fifth fluid port are in direct fluid connection to the fluid chamber, the direct fluid connection being located between the first longitudinal end of the first sealing means and the second longitudinal end of the second sealing means.

19. The system according to claim 3 further comprising a sixth fluid port arranged at the second compartment of the first lid, the sixth fluid port being closed by a closing means.

* * * * *